United States Patent
Bitar et al.

(10) Patent No.: US 7,368,279 B2
(45) Date of Patent: May 6, 2008

(54) THREE DIMENSIONAL BIOENGINEERED SMOOTH MUSCLE TISSUE AND SPHINCTERS AND METHODS THEREFOR

(75) Inventors: Khalil N. Bitar, Ann Arbor, MI (US); Louise Hecker, Ann Arbor, MI (US); Keith Baar, Dundee (GB); Sita Somara, Ypsilanti, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 238 days.

(21) Appl. No.: 11/286,544

(22) Filed: Nov. 23, 2005

(65) Prior Publication Data

US 2006/0134076 A1  Jun. 22, 2006

Related U.S. Application Data

(60) Provisional application No. 60/630,816, filed on Nov. 24, 2004.

(51) Int. Cl.
*A61F 2/00* (2006.01)
*C12M 3/00* (2006.01)
*C12M 1/22* (2006.01)

(52) U.S. Cl. .................. 435/284.1; 600/29; 435/298.3

(58) Field of Classification Search .................. 600/29; 435/284.1, 288.3
See application file for complete search history.

(56) References Cited

U.S. PATENT DOCUMENTS

| | | | |
|---|---|---|---|
| 4,505,266 | A | 3/1985 | Yannas et al. |
| 5,190,878 | A | 3/1993 | Wilhelm et al. |
| 5,231,169 | A | 7/1993 | Constantz et al. |
| 5,605,835 | A | 2/1997 | Hu et al. |
| 5,688,687 | A | 11/1997 | Palsson et al. |
| 5,888,807 | A | 3/1999 | Palsson et al. |
| 5,985,653 | A | 11/1999 | Armstrong et al. |
| 6,001,642 | A | 12/1999 | Tsao |
| 6,096,532 | A | 8/2000 | Armstrong et al. |
| 6,659,936 | B1 * | 12/2003 | Furness et al. ............. 600/30 |

OTHER PUBLICATIONS

Badybak et al., *J. Surg. Res.*, 47:74-80 (1989).
Bitar et al., *Am. J. Physiol.*, 242:G400-G407 (1982).
Bitar et al., *Am. J. Physiol.*, 250:G357-G360 (1986).
Bitar et al., *Am. J. Physiol.*, 260:G537-G542 (1991).
Bitar et al., *Am. J. Physiol.*, 282:G894-G903 (2002).
Bitar et al., *Am. J. Physiol.*, 284:G1-G7 (2003).
Bitar et al., *Life Sci.*, 47:2429-2434 (1990).
Bitar et al., *Science*, 216:531-533 (1982).
Blank et al., *J. Cell. Biol.*, 107:299-306 (1988).
Carson, *Histotechnology: A Self-Instructional Text*, Chicago: American Society for Clinical Pathology Press (1997), table of contents.
Chakder et al., *Am. J. Physiol.*, 264:G702-G707 (1993).
Chalovich, *Pharmacology & Therapeutics*, 55:95-148 (1992).
Chu et al., *Gene*, 13:197-202 (1981).
Davis et al., *Basic Methods in Molecular Biology*, Elsevier (1986), table of contents.
Delechenaut et al., *Dis. Colon Rectum*, 35:847-849 (1992).
Dennis et al., *American Journal of Physiology Cell Physilogy*, 280:C288-C295 (2001).
Dennis et al., *In Vito Cellular & Developmental Biology Animal*, 36:327-335 (2000).
Dukan et al., *Proc. Natl. Acad.*, 97:5746-5749 (2000).
Edelman, *Circ. Res.*, 85:1115-1117 (1999).
Freshney, *Culture of Animal Cells*, Wiley-Liss Inc., New York (1994), table of contents.
Freshney, *Culture of Animals Cells. A Manual of Basic Technique*, 2d Ed., A.R. Liss, Inc., New York, Ch. 9, p. 107-126 (1987).
Freshney, *Culture of Animals Cells. A Manual of Basic Techniques*, 2d Ed., A.R. Liss, Inc., New York, Ch. 11, p. 137-168 (1987).
Glavind et al., *American Journal of Physiology Gastrointestinal and Liver Physiology*, 265:G792-G798 (1993).
Glavind et al., *American Journal of Physiology Gastrointestinal and Liver Physiology*, 272:G1075-G1082 (1997).
Goeddel, *Gene Expression Technology: Methods in Enzymology 185*, Academic Press, San Diego, CA (1990), table of contents.
Gorenne et al., *Am. J. Physiol.*, 5:H131-H138 (1998).
Goyal et al., *The Gastriontestinal System, Motility and Circulation*, in *Handbook of Physiology*, J.D. Wood and S.G. Schultz, Editors, p. 865-908 (1989).
Goyal, *N. Engl. J. Med.*, 321:1022-1029 (1989).
Grassl et al., *Journal of Biomedical Material Research*, 60:607-612 (2002).

(Continued)

*Primary Examiner*—Maryam Monshipouri
(74) *Attorney, Agent, or Firm*—Marshall, Gerstein & Borun LLP

(57) ABSTRACT

This invention relates to a three dimensional bioengineered sphincter such as a bioengineered internal anal sphincter (IAS) and three-dimensional physiological models of smooth muscle cells. The invention also related to methods for generating a bioengineered sphincter and smooth muscle rings in culture. In addition, the invention provides for methods of using a bioengineered sphincter or bioengineered smooth muscle ring to identify agents that modify contractile force and relaxation in smooth muscle cells.

4 Claims, 5 Drawing Sheets

OTHER PUBLICATIONS

Grassl et al., *Journal of Biomedical Materials Research*, 66A:550-561 (2003).
Horowitz et al., *Physiological Reviews*, 76:967-1003 (1996).
Humason, *Animal Tissue Techniques*, Baltimore: John Hopkins University Press (1997), table of contents.
Hungerford et al., *Developmental Biology*, 178:375-392 (1996).
Janis et al., *J. Pharmacol. Exp. Ther.*, 211:480-484 (1979).
Jones et al., *Can. J. Physiol. Pharmacol.*, 16:249-257 (2002).
Knudsen et al., *Am. J. Physiol.*, 269:G232-G239 (1995).
Lam, *Anticancer Drug Des.*, 12:145-167 (1997).
Langer et al., *Nature*, 263:797-800 (1976).
Laurberg et al., *Dis. Colon Rectum*, 32:737-742 (1989).
Lavoie et al., *Mol. Cell. Biol.*, 15:505-516 (1995).
Macpherson et al., *J. Physiol.*, 500:523-533 (1997).
Matsufuji et al., *Journal of Smooth Muscle Research*, 39:11-20 (2003).
Morimoto, *Cell*, 110:281-284 (2002).
Moummi et al., *American Journal of Physiology Gastrointestinal and Liver Physiology*, 255:G571-G578 (1988).
Napoli et al., *Biochemistry*, 19:2515-2521 (1980).
Nardai et al., *Exp. Gerontology*, 37:1257-1262 (2002).
Neidert et al., *Biomaterials*, 17:3717-3731 (2002).
Nelson et al., *JAMA*, 274:559-561 (1995).
Patil et al., *Am. J. Physiol.*, 286:G635-G644 (2004).
Perry et al., *Gut*, 50:480-484 (2002).
Ross et al., *Matrix Biology*, 22:477-490 (2003).
Rossman et al., *Dig Dis. Sci.*, 38:1569-1580 (1993).
Ryazanov et al., *Mechanisms of Ageing and Development*, 123:207-213 (2002).
Schafer et al., *Am. J. Physiol.*, 277:C1032-C1043 (1999).
Somara et al., *Am. J. Physiol.*, 286:C1290-C1301 (2004).
Soti et al., *Exp. Gerontology*, 38:1037-1040 (2003).
Stadtman et al., *Drug Met. Rev.*, 30:225-243 (1998).
Sultan et al., *British Medical Journal*, 308:887-891 (1994).
Sun et al., *Gastroenterology*, 97:130-135 (1989).
Szymanski et al., *Am. J. Physiol.*, 282:C94-C104 (2002).
Talley et all., *Gastroenterology*, 102:895-901 (1992).
Valdivia, *Curj.*, 1:6-11 (2001).

* cited by examiner

Figure 1
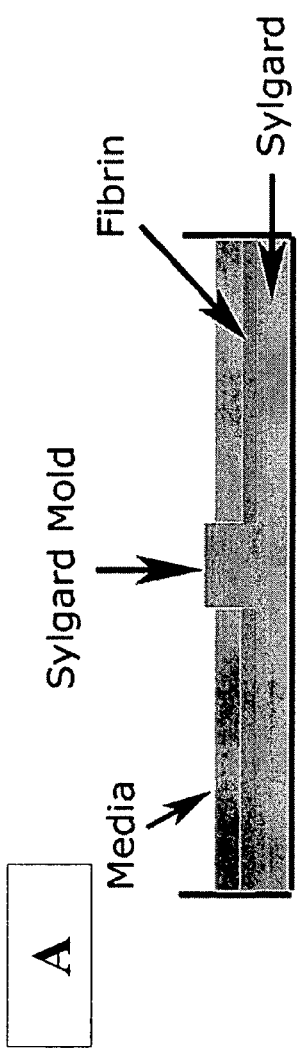
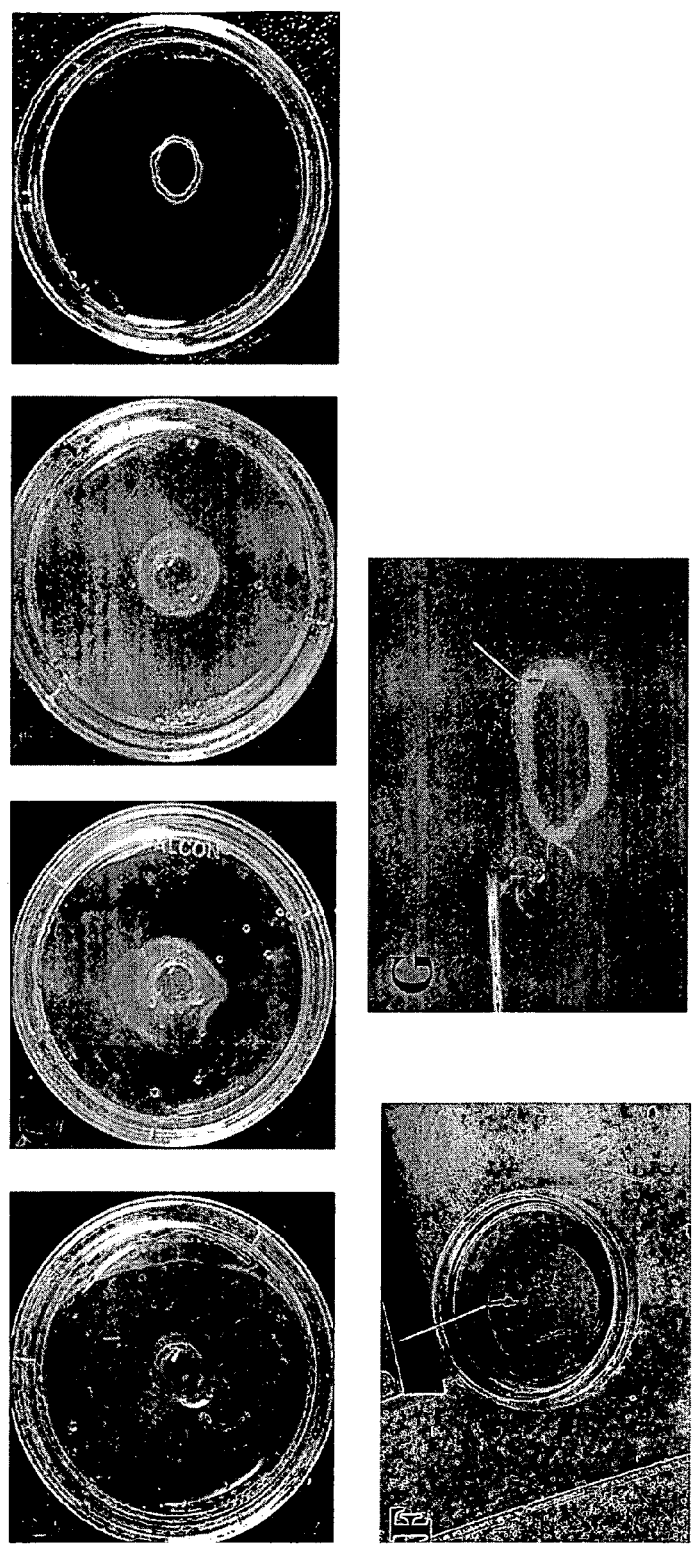

Figure 5
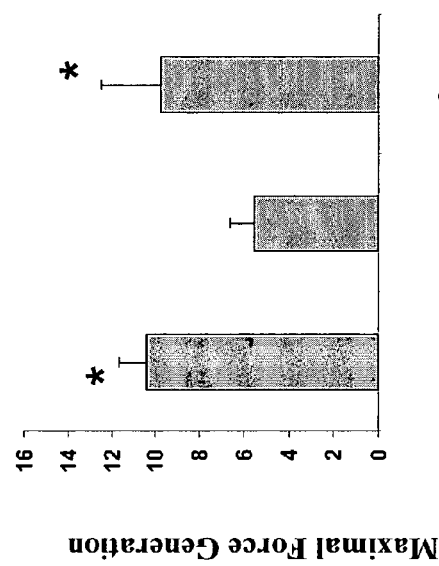
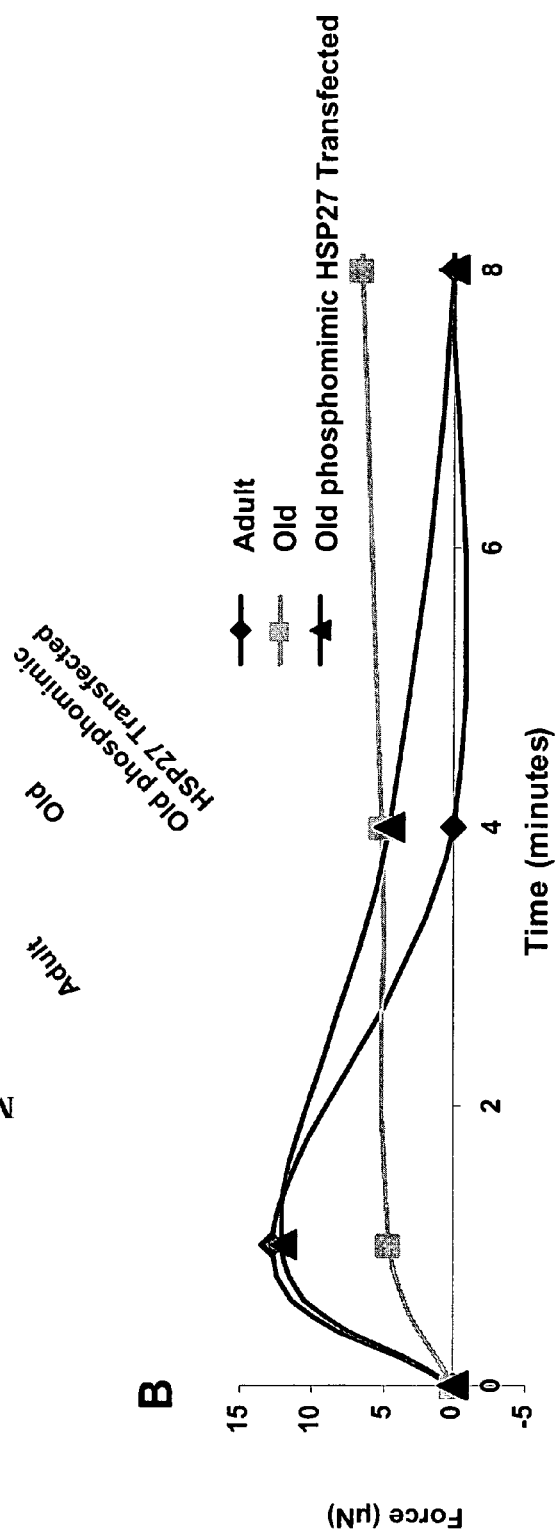

THREE DIMENSIONAL BIOENGINEERED SMOOTH MUSCLE TISSUE AND SPHINCTERS AND METHODS THEREFOR

RELATED APPLICATIONS

The present application claims priority benefit of U.S. Provisional Application No. 60/630,816 filed Nov. 24, 2004 which is herein incorporated by reference in its entirety.

Scientific work relating to the invention was supported by Grant No. DK-042876 from the United States National Institute of Diabetes and Digestive and Kidney Diseases. The United States government may have certain rights in the invention.

FIELD OF THE INVENTION

This invention relates to a three dimensional bioengineered smooth muscle cell ring and a three dimensional bioengineered sphincter such as a bioengineered internal anal sphincter (IAS). The invention also related to methods for generating a bioengineered sphincter in culture and methods of using a bioengineered sphincter to identify agents that modify contractile force and relaxation in smooth muscle cells.

BACKGROUND

Sphincter malfunction results from sluggish contractile response of the skeletal and smooth muscle of the sphincter. In the basal state, the smooth muscle of the sphincter remains in a state of tonic contraction and closure to serve as a one-way valve to regulate flow through the opening controlled by the sphincter. Skeletal muscle sphincters are under voluntary control while smooth muscle sphincters are controlled by complex interactions between extrinsic nerves from the central nervous system (CNS) and intrinsic control by the enteric nervous system and the myogenic properties of specialized smooth muscle cells.

Sphincteric smooth muscles represent tonic muscles that remain contracted at rest and have small amplitude, slow contraction and slow relaxation response, while non-sphincteric smooth muscle represent phasic muscle that shows a wide range of contractile activity varying from a fully relaxed basal state to a large-amplitude rapid contraction and rapid relaxation response (Goyal et al., *The Gastrointestinal System, Motility and Circulation*, in *Handbook of Physiology*, J. D. Wood and S. G. Schultz, Editors. 1989, The American Physiological Society: Bethesda. p. 865-908). It has been reported that tonic muscle may have lower levels of myosin light chain kinase and myosin light chain phosphatase than phasic muscle (Horowitz et al., *Physiological Reviews*, 76(4): p. 967-1003, 1996). The main contractile proteins are actin and myosin. The actin-binding proteins, such as tropomyosin, calponin and caldesmon, play a role in the thin filament based regulation of smooth muscle contractility (Reviewed in Chalovich, *Pharmacology & Therapeutics*, 55(2): 95-148, 1992).

Tissue culture was developed in the early 1900's as a technique for studying the behavior of animal cells in vitro. Advances in technology have led to the use of tissue culture for studying many areas of cellular function including intracellular activity, intracellular flux, environmental interaction, cell-cell interaction, and genetics. (Freshney, *Culture of Animal Cells*. New York: Wiley-Liss Inc, 1994) However, two-dimensional cell culture provides few options to study contractile force production as a cellular function. Furthermore, cells which are propagated and tested two-dimensionally are not exposed to cellular and environmental cues that may play a role in differentiation and the establishment of normal physiological function. Isolation of single cells and cell suspensions has enabled biochemical and mechanical measurements at the cellular level and has advanced the understanding of smooth muscle function. (Bitar et al., *Am J Physiol*. 260: G537-G542, 1991) Yet, cell suspensions also lack the potential for cell-cell interactions and cell-matrix interactions which are provided by three-dimensional tissues. (Freshney, *Culture of Animal Cells*. New York: Wiley-Liss Inc, 1994) It is well known that physiological functions of tissues are retained when the three-dimensional structure is kept intact. (Hungerford et al., *Developmental Biology* 178: 375-392, 1996) Isolated tissues and organ preparations, such as muscle strips, provide researchers with a three-dimensional tissue that may be subjected to controlled changes in perfusion, oxygen availability, and agonist-induced stimulation (Glavind et al., *Am J Physiol*. 265: G792-G798, 1993; Glavind et al., *Am J Physiol*. 272: G1075-G1082, 1997; Knudsen et al., *Am J Physiol*. 269: G232-G239, 1995). Despite the obvious advantages of tissue/organ explants, many limitations remain. Explanted tissues are composed of several different cell types, for example, muscle strips from the internal anal sphincter may be comprised of smooth muscle, and any combination of mucosal, epithelial, and/or neuronal cells. In addition, explanted tissues do not survive indefinitely and are usually only viable for up to four hours after isolation. This short-term viability prevents long-term investigation, and requires the explants be prepared de novo for each experiment. Damage to the tissue and/or release of material from damaged erythrocytes occurring during dissection also inhibits the ability to produce normal functionality and environmental conditions. Lastly, tissue/organ explants must be placed in a cold (usually 4° Celsius) buffer or bath to prevent rapid degradation.

Due to the limitations of investigating explant, tissue engineering has emerged as a valuable tool that applies the principles of engineering and life sciences toward the development of biological models with characteristics similar to those observed in vivo. Specific cell types can be isolated and bioengineered to yield a homogenous tissue. In addition, bioengineered tissues can be maintained in culture for long periods of time under physiological conditions. Advances in tissue engineering have been clinically applied to restore, maintain, and improve tissue function (Edelman, *Circ Res*. 85: 1115-1117, 1999; Valdivia, *Curj* 1: 6-11, 2001).

SUMMARY OF INVENTION

There is a need for the development of functional in vitro models of sphincters that may be used to elucidate the mechanisms causing smooth muscle degenerative diseases. The fibrin-based constructs of the invention provide the opportunity to test the effects of various pharmacological agents, growth factors, and mechanical interventions on smooth muscle function. The bioengineered sphincters of the invention provide a functional in vitro sphincter model that may be used to elucidate the mechanisms causing smooth myogenic sphincter malfunction as well as the investigation of treatments for disorders relating to sphincter dysfunction and/or weakening of smooth muscle contractile force.

The present invention is directed to a bioengineered sphincter comprising smooth muscle cells that contract in response to an agonist of contraction and methods of generating the bioengineered sphincter in vitro. An agonist of contraction is any agent that induces or increases a contractile response in a smooth muscle cell or any agent that induces electrical stimulation of a smooth muscle cell. Contractile response is defined as the decrease in the average length of a smooth muscle cell or smooth muscle tissue. Agonists of contraction may be any compound that induces electrical stimulation such as, bombesin, substance P, protein kinase C (PKC), endothelins, peptides and neurotransmitters such as acetylcholine. The bioengineered sphincter may be generated by culturing smooth muscle cells in a cell culture vessel containing a cylindrical mold coated with an extracellular matrix protein, such as fibrin.

Particular methods of generating a sphincter ring in vitro comprise coating a cell culture vessel containing a cylindrical mold with a polymer, covering the polymer coated vessel with one or more extracellular matrix proteins, and growing smooth muscle cells in the cell culture vessel under condition in which the smooth muscle cells reorganize to form parallel arrays of cells and the smooth muscle cells contract in response to an agonist. The smooth muscle cells may be grown in the extracellular matrix coated vessel by layering the cells on the extracellular matrix or by mixing the cells within the extracellular matrix. In a preferred embodiment, the cell culture vessel and cylindrical mold is coated with a silicone elastomer such as polydimethyl siloxane (PDSM) which is subsequently coated with extracellular matrix protein fibrin.

The invention also provides for method of identifying agents that modulate smooth muscle cell contraction and relaxation, in particular, sphincter contraction and relaxation. These methods comprise contacting a bioengineered sphincter of the invention or a ring of circular smooth muscle cells, generated by the methods described herein, with an agonist of contraction. Then measuring changes in peak isometric contraction of the smooth muscle cells of the sphincter in response to the agonist of contraction in the presence and absence of the test agent and comparing the change in peak isometric force in the presence and absence of the test agent. In one embodiment, the test agent is added to the sphincter exogenously. In another embodiment, the smooth muscle cells used to generate the sphincter are transfected with the test agent and will express the test agent. In the methods, the changes in peak isometric contraction are compared to the change in peak isometric contraction in sphincters generated with smooth cells that do not express the test agent.

Preferably, the methods of identifying an agent that modulates smooth muscle cell contraction or sphincter contraction comprise stretching the sphincter or smooth muscle cells to approximately 50% of its resting length, measuring base line force of smooth muscle contraction in the presence and absence of the test agent, measuring isometric force in response to an agonist, such as acetylcholine, in the presence and absence of the test agent, and comparing the change in isometric force in the smooth muscle cells or the sphincter in the presence and absence of a test agent. An increase in the change in isometric force in the presence of the test agent identifies the agent as a stimulator of smooth muscle cell contraction or a stimulator of sphincter function. A decrease in the change in isometric force in the presence of a test agent identifies the agent as an inhibitor of smooth muscle cell contraction or an inhibitor of sphincter function.

The agents identified as stimulators of smooth muscle cell contraction are contemplated as potential therapeutics for disorders relating to sphincter dysfunction caused by age-related factors and/or decreased smooth muscle contractile force. These disorders include fecal incontinence, gastroesophageal reflux disease, urinary incontinence and biliary dyskinesia in name a few.

The invention also provides methods of treating disorders relating to sphincter dysfunction comprising administering a modulator of smooth muscle cell contraction identified by the methods of the present invention in an amount effective to increase or decrease smooth muscle cell contractile force to a mammal in need thereof. The invention also provides methods of replacing a defective sphincter by implanting a bioengineered sphincter of the present invention in a mammal in need. The invention further provides pharmaceutical compositions comprising modulators of smooth muscle cell contraction identified by the methods of the invention.

The invention provides for methods of generating bioengineered smooth muscle rings. The invention also contemplates using the culture system described herein to generate three-dimensional physiological models of smooth muscle tissue using smooth muscle cells isolated from any tissue or organ that contains circular smooth muscle. The invention contemplates bioengineered smooth muscle rings and smooth muscle models that retain the tissue-specific genetic preprogramming of the isolated tissue or organ. In addition, it is contemplated that the bioengineered smooth muscle rings and smooth muscle models exhibit the physiological function of the organ or tissue from which the smooth muscle was isolated.

The invention further provides for methods of co-culturing the smooth muscle cells and embryonic nerve cells or stem cells to form bioengineered rings of smooth muscle. For example, co-cultures of colon smooth muscle with embryonic nerve cells using the culture methods of the invention to create bioengineered colon rings that are useful for the identification of treatments of colonic disorders such as Hirschsprung's Disease. In addition, airway smooth muscle cells may be cultured using the methods of the invention to create bioengineered airway smooth muscle rings which will be useful for the identification of treatments for bronchial diseases such as asthma.

In one aspect, methods of the present invention identified chaperone protein heat shock protein 27 (HSP27) as a stimulator of smooth muscle cell contraction. In particular, phosho-HSP27 reinstates the contractile force of aged smooth muscle cells and bioengineered sphincters generated with aged smooth muscle cells. As described in detail in Example 4, phosho-HSP27 restored contractile response in bioengineered internal anal sphincter (IAS) rings that comprise smooth muscle cells from aged rats. Thus, phospho-HSP27 may be a therapeutic for reinstating the contractile force in sphincters that dysfunction or weaken with increasing age. The invention also provides methods of stimulating or reinstating smooth muscle contractile force comprising administering phosphor-HSP27 in an amount effective to increase or regenerate smooth muscle contractile force to a mammal in need. The invention also provides methods of treating age-related disorders associated with sphincter dysfunction comprising administering phosphor-HSP27 or pharmaceutical compositions comprising phospho-HSP27 in an amount effective to induce or regenerate smooth muscle contraction.

BRIEF DESCRIPTION OF FIGURES

FIG. 1 depicts the cell culture vessel used to generate the three-dimensional bioengineered sphincters. Panel A depicts a schematic of a vessel (35 mm dish shown) containing a cylindrical mold coated with a polymer such as SYLGARD (polydimethylsiloxane-PDMS). The vessel was then coated with extracellular matrix protein (fibrin is shown). Panels B-E depict the progression of fibrin gel to the formation of the three-dimensional bioengineered sphincter. Panel E depicts the fully formed bioengineered sphincter. Following ring formation, the bioengineered sphincter was released from its mold before mechanical testing. Panels F-G depict the mechanical testing of the three-dimensional bioengineered sphincter. The construct was placed on an aluminum heating plate and prepared for mechanical testing (panel F). Panel G is an enlarged view of panel F. Following release from its mold, the bioengineered sphincter was secured to the polymer substrate using a stainless steel pin (right side of panel G). The opposite end was attached to a hook-shaped stainless steel pin and then attached to the force transducer using canning wax (left side of panel G).

FIG. 5 depicts the effect of phospho-HSP27 transfection on reinstatement of maximal force generation and time-to-peak response in IAS rings. Panel A depicts measurement of maximum force generated by bioengineered IAS rings made from adult, old, and old phosphomimic-HSP27 transfected rings. Maximum force generated by bioengineered IAS rings from old rats was significantly less as compared to bioengineered IAS ring from adult rat (old: 5.5±1.09, n=4; adult: 10.4±1.27, n=3; P<0.01). Bioengineered IAS rings from phosphomimic-HSP27 transfected old sphincteric smooth muscle cells showed reinstatement of maximal force generation which was significantly different from the age-matched bioengineered IAS rings (old phospho-HSP27 transfected: 9.7±2.75, n=3; old: 5.5±1.09, n=4; P<0.05). Panel B graphs data points representing four successive readings of the force generated (contraction) by adult, old, and old phosphomimic-HSP27 transfected IAS rings upon the addition of $10^{-6}$M acetylcholine. Maximum force generated by old bioengineered IAS rings was approximately 3-fold less than adult IAS rings. Phosphomimic-HSP27 transfected old IAS rings showed reinstatement of maximal force generation that was similar to adult IAS rings, as well as a dramatic decrease in time-to-peak contraction compared to old IAS rings.

DETAILED DESCRIPTION

Figure 2:
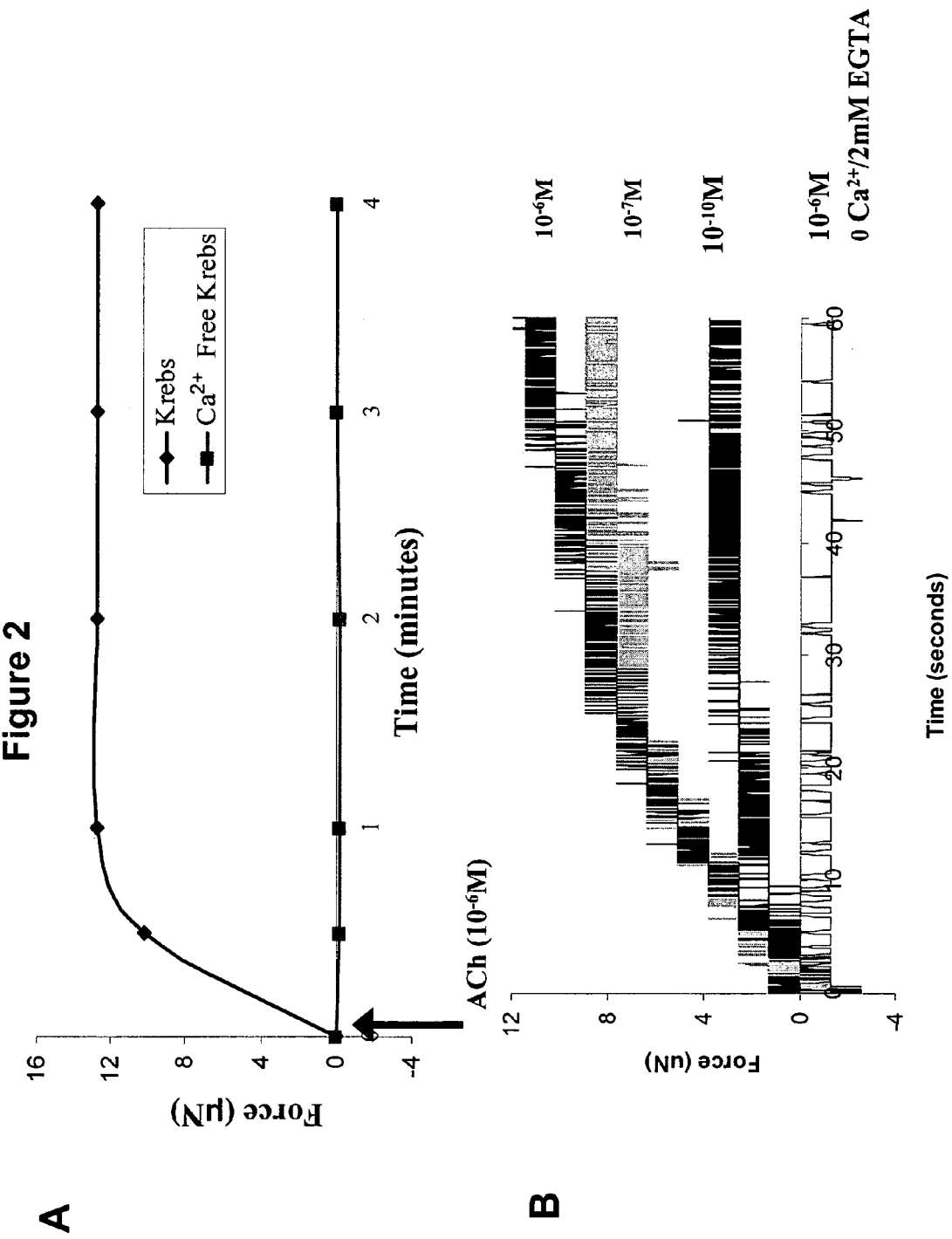
FIG. 2 depicts the effect of $10^{-7}$M acetylcholine on bioengineered internal anal spincter (IAS) rings in Krebs buffer versus 0 $Ca^{2+}$/2 mM EGTA Krebs buffer Panel A depicts Data points representing five successive readings of the force generated by IAS rings following the addition of acetylcholine to IAS constructs in Krebs and in 0 Ca2+/2 mM EGTA Krebs buffer. IAS rings showed a peak contraction at one minute in Krebs buffer which was sustained for 4 minutes. IAS rings in 0 Ca2+/2 mM Krebs demonstrated no contraction after the addition of acetylcholine. Panel B is a graph representing details of the kinetics of bioengineered IAS rings following stimulation with acetylcholine within the first minute. Increasing doses of acetylcholine resulted in increased force production.

The invention provides bioengineered sphincters comprising functional smooth muscles cells. The term "smooth muscle ring" refers to the arrangement of smooth muscle cells into a circumferential alignment. The term "sphincter" refers to a ring-like band of smooth muscle fibers that constricts a passage or closes a natural orifice, also known as a musculus sphincter. The term "bioengineered" refers to the development and manufacture of non-naturally occurring tissues and organs, such as generating tissue in cell culture.

Visceral smooth muscles have been classified into sphincteric and non-sphincteric smooth muscles that represent tonic and phasic muscles (Horowitz et al., *Physiol. Rev.*, 76(4): p. 967-1003, 1996; Goyal, *N. Engl. J. Med.*, 321(15): p. 1022-9, 1989; Szymanski et al., *Amer. J. Physiol.* 282(1): p. C94-C104, 2002). Phasic muscle shows a very wide range of contractile activity that varies from a fully relaxed basal state to a large-amplitude rapid contraction and rapid relaxation response. In contrast, tonic muscles remain contracted at rest and have small amplitude slow contraction and slow relaxation response (Goyal & Paterson, *The Gastrointestinal System, Motility and Circulation, in Handbook of Physiology*, J. D. Wood and S. G. Schultz, Editors. 1989, The American Physiological Society: Bethesda. p. 865-908) While non-sphincteric visceral smooth muscle consists of circular smooth muscle surrounded by longitudinal smooth muscle, sphincteric smooth muscle consists only of circular smooth muscle. Sphincteric smooth muscles are highly specialized and are located in areas with significant contracture and specialized functions.

Bioengineered Sphincters and Smooth Muscle Rings

The invention provides methods of generating bioengineered sphincters, smooth muscle rings and physiological models of smooth muscle tissue that contract in response to an agonist of contraction, such as acetylcholine. As describe in Example 2, fibrin gel casting was used to develop a three-dimensional model of an internal anal sphincter (IAS) using isolated rabbit smooth muscle cells. The bioengineered sphincters of the invention formed in approximately 10 days and were functionally similar to gastrointestinal (GI) smooth muscle in vivo for up to 40 days. When stimulated with acetylcholine, the IAS rings produced a calcium-dependent maximal force of 9.8±3.8 μN. Stimulation with $10^{-5}$M 8-br-cAMP resulted in a calcium-independent relaxation of −16.3±2.0 μN from the basal tone. In an embodiment of the invention, the bioengineered sphincters form around a cylindrical mold within a cell culture vessel. The cylindrical mold and the vessel may be coated with a polymer such as polydimethyl siloxane (PDSM). Example 5 describes a bioengineered three dimensional physiological model of smooth muscle tissue generated with isolated colon smooth muscle. The three dimensional model of colon smooth muscle demonstrated physiological functionality, including spontaneous contractile behavior and contraction in response to an agonist of contraction, acetylcholine.

The invention encompasses generating bioengineered sphincters that are functionally similar to any naturally occurring mammalian sphincter. Human gastrointestinal sphincters include the cardiac sphincter (gastroesophageal) which is the junction between the esophagus and the stomach. The cardiac sphincter is further characterized as the lower esophageal sphincter (LES) and the upper esophageal sphincter (UAS). Gastrointestinal sphincters also include the pharyngoespageal sphincter, which is the junction between the pharynx and the esophagus that is involved in swallowing, the pyloric sphincter, which is the junction between the stomach and the duodenum, the ileocolonic sphincter, the sphincter of the bile duct (also known as the sphincter of Oddi or choledochal sphincter), which is the junction between bile duct and main pancreatic duct and the small intestine, the sphincter of Boyden, and the Lukens' sphincter, which is a thickening of the muscle fibers in the neck of the gall bladder, the rectal spincter or Hyrtl's sphincter, and the internal anal sphincter and the external anal sphincter (EAS). Human uritogenital tract sphincters include the urethral sphincter, which controls the flow of urine from the urinary bladder, the vaginal sphincter, which keeps the vagina closed, the tubal sphincter which is the junction between the uterine tube and the uterus, Henle's sphincter, which surrounds the prostatic urethra, and the inguinal sphincter, which is a ring of muscle fibers around the spermatic cord at the internal opening of the inguinal canal. Human sphincters also include the larynx, which is the sphincter that guards entrance into the trachea, the palatopharyngal sphincter, which is a thickening of the muscle fibers in the posterior wall of the pharynx that contracts during swallowing, and the hepatic sphincter which is a thickening of the muscular coat of the hepatic veins near the entrance into the inferior vena cava.

In particular, the internal anal sphincter (IAS) is a specialized circular smooth muscle with elevated basal tone as compared to the rectum, which plays a significant role in recto-anal continence. The IAS is characterized by its ability to maintain tone and to relax, allowing the passage of feces. Although the major tone is due to the myogenic properties, a number of neurohumoral and hormonal responses of the muscle cells also cause the tone in the IAS. In the canine IAS, the mechanical responses of smooth muscle are modulated by alpha-adrenergic excitatory and non-adrenergic, non-cholinergic inhibitory nerves (Matsufuji et al., Journal of Smooth Muscle Research, 39(1-2): p. 11-20, 2003).

The invention also encompasses generating bioengineered smooth muscle rings and physiological models of smooth muscle tissues other than sphincters that are functionally similar to any naturally occurring smooth muscle tissue. Any organs or tissue that contains circular smooth muscle may be modeled using the culture system of the invention. Such organs and tissues include the esophagus, stomach, duodenum, jejumen, ileum, colon, trachea, bronchial tubes, uterus, blood vessels, lymphatic vessels, urethra, glandular ducts, and the ciliary muscle of the eye.

The term "functionally similar" refers to a bioengineered sphincter or bioengineered smooth muscle rings having similar contractile force or a similar change in contractile isometric force to natural sphincters. Contractile force is measured in response to an agonist of smooth muscle contraction. An agonist of contraction is any agent that induces a contractile response in a smooth muscle cell or induces electrical stimulation in a smooth muscle cell. Contractile response is defined as the decrease in the average length of a smooth muscle cell or smooth muscle tissue. Agonists of contraction include acetycholine, bombesin, substance P, protein kinase C (PKC), endothelins, other neurotransmitter and peptides.

In another embodiment, smooth muscle cells transfected to express phosphorylated HSP27 or phosphomimic HSP27 (both denoted herein as "phospho-HSP27") or a modulator of smooth muscle cell contraction or relaxation may be used to generate bioengineered sphincters of the invention. In addition, the bioengineered sphincters of the invention may be generated in co-cultures comprising embryonic nerve cells or stem cells, which are transfected to express a modulator of smooth muscle cell contraction or relaxation such as HSP27. A number of transfection techniques are well known in the art such as calcium phosphate transfection, DEAE, dextran mediated transfection, lipofectamine transfection or electroporation (Davis et al., *Basic Methods in Molecular Biology*, 1986; Sambrook et al., *Molecular Cloning, a laboratory Manual*, Cold Spring Harbor Laboratories (New York, 1989); Davis et al., *Basic Methods in Molecular Biology*, Elsevier, 1986; and Chu et al., *Gene*, 13:197, 1981).

In addition, the methods of the present invention may be carried out with smooth cells transfected to express phospho-HSP27 or a modulator of smooth muscle cell contraction or relaxation. For a cell to be used in the methods of the invention, the cell must endogenously be transfected to express a smooth muscle cell contraction modulator, such as HSP27. The invention provides for nucleic acid constructs containing a nucleic acid molecules that encode these polypeptides. The constructs comprise a vector (e.g., an expression vector) into which one or more smooth muscle cell modulators have been inserted in a sense or antisense orientation. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, expression vectors, are capable of directing the expression of genes to which they are operably linked. In general, expression vectors of utility in recombinant DNA techniques are often in the form of plasmids. However, the invention is intended to include such other forms of expression vectors, such as viral vectors (e.g., replication defective retroviruses, adenoviruses and adeno-associated viruses) that serve similar functions.

Preferred recombinant expression vectors comprise a nucleic acid molecule that encodes a desired polypeptide in a form suitable for expression of the polypeptide in a host cell. Therefore, recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). The design of the expression vector can depend on such factors as the choice of the host cell to be transformed and the level of expression of polypeptide desired. The expression vectors can be introduced into host cells to thereby produce polypeptides, including fusion polypeptides, encoded by nucleic acid molecules as described herein.

Another aspect of the invention pertains to host cells into which a recombinant expression vector of the invention has been introduced. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. Aspects of the invention described by reference to a cell should be understood to embrace embodiments using multiple cells.

Vector DNA can be introduced into an eukaryotic cell via conventional transformation or transfection techniques. As used herein, the term "transfection" is intended to refer to a variety of art-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. *Molecular Cloning, a laboratory manual*, Cold Spring Harbor Laboratories (New York, 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Nucleic acid molecules encoding a selectable marker can be introduced into a host cell on the same vector as the nucleic acid molecule of the invention or can be introduced on a separate vector. Cells stably transfected with the introduced nucleic acid molecule can be identified by drug selection (e.g., cells that have incorporated the selectable marker gene will survive, while the other cells die).

In designing a bioengineered sphincter the following parameters must be considered: three-dimensionality, potential for cell-cell and cell-matrix interactions, enhanced viability, and maintenance under physiological conditions in a controlled environment.

Smooth Muscle Cells

Smooth muscle surrounds the supports of many of the hollow organs. For example, in the gut smooth muscle surrounds the stomach and intestinal track. Contraction of this muscle mixes food and propels it along the digestive track. In the cardiovascular system, smooth muscle cells surround the walls of the arteries and large veins and functions to control the caliber of the vessels. Smooth muscle lacks the nearly uniform cell shape and lattice-like distribution of skeletal and cardiac muscle cells. However, smooth muscle cells do exhibit an elongated, bipolar cell shape. As a population, smooth muscle cells are organized along a similar axis in a series of overlapping cellular layers. This pattern of organization allows smooth muscle to exert contractile forces in a complex pattern.

The present invention can be employed using isolated primary smooth muscle cells as described in detail in Example 1 or cell lines derived from such primary cells, tumors and the like. The cells used may be available smooth muscle cell lines such as internal anal sphincter smooth muscle cell lines, airway smooth muscle cell lines and other commercially available smooth muscle cell lines. For example, cell lines derived from muscle may be obtained from a cell line depository such as the American Type Culture Collection (ATCC, Bethesda, Md.). Such cell smooth muscle cell lines include human iliac vein smooth muscle cells (HIVS-125; ATCC accession no. CRL-2482), Syrian Golden Hamster ductus deferens smooth muscle cells (DDT1; CRL-1701), human umbical vein smooth muscle cells (HUVS-112D: CRL-2481), rat aorta smooth muscle cells (Hep-Sa; CRL-2018), and human aortic smooth muscle cells (T/G HA-VSMC; CRL-2498). The conditions for growth of the specific cell line purchased will depend on the biological source and generally instructions for the growth of the cells are made available along with the cell lines from ATCC.

In one aspect, the cell lines are able to differentiate into cells that possess contractile function. The cells may be derived from any vertebrate or non-vertebrate animal source. For example, the animal source may be human, monkey or other primate, mouse, rat, rabbit, cat, dog, goat, sheep, pig, horse, cow, fish, bird or any other animal from which such cells may be harvested. In one aspect, the smooth muscle cells used in the three-dimensional culture are mammalian cells. In another aspect, the cells are human or primate cells, but rat and rabbit cells also will be usefully employed herein. The appropriate growth factors may be added to the culture. The concentration of such factors maintained in the cultures can be monitored and adjusted to optimize growth. Cells cultured in this manner can be used for transplantation or implantation in vivo. In such cases, it is preferable to obtain the muscle cells from the patient's own tissues.

The invention may be carried out with primary smooth muscle cells isolated from a variety of organs which contain circular smooth muscle. Organs that contain circular smooth muscle include the esophagus, stomach, duodenum, jejumen, ileum, colon, trachea, bronchial tubes, uterus, blood vessels, lymphatic vessels, urethra, glandular ducts, and the ciliary muscle of the eye. The primary cells may be readily isolated by disaggregating an appropriate organ or tissue which is to serve as the source of the cells being grown using standard techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. The digestive enzymes include but are not limited to trypsin, chymotrypsin, collagenase, elastase, and/or hyaluronidase, DNase and pronase. Mechanical disruption can also be accomplished by a number of methods including, but not limited to the use of grinders, blenders, sieves, homogenizers, pressure cells, or sonicators to name but a few. For a review of tissue disaggregation techniques, see Freshney, *Culture of Animal Cells. A Manual of Basic Technique*, 2d Ed., A. R. Liss, Inc., New York, 1987, Ch. 9, pp. 107-126.

Once the tissue has been reduced to a suspension of individual cells, the suspension can be fractionated into subpopulations from which the myocyte and/or fibroblast cells can be obtained. Fractionation also may be accomplished using standard techniques for cell separation including but not limited to cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counter-streaming centrifugation), unit gravity separation, counter current distribution, electrophoresis and fluorescence-activated cell sorting. For a review of clonal selection and cell separation techniques, see Freshney, *Culture of Animal Cells. A Manual of Basic Techniques*, 2d Ed., A. R. Liss, Inc., New York, 1987, Ch. 11 and 12, pp. 137-168.

To generate the three-dimensional sphincters in culture, the cells must be grown in an appropriate nutrient medium. Many commercially available media such as DMEM, RPMI 1640, Fisher's Iscove's, McCoy's, and the like may be suitable for use. In addition, the three-dimensional cultures should be "fed" periodically to remove the spent media and depopulate released cells.

These procedures are greatly facilitated when carried out using a bioreactor, which is a closed system housing the three-dimensional framework inoculated with muscle cells. A bioreactor reduces the possibility of contamination, maintains the cultures under intermittent and periodic pressurization to create environmental conditions that maintain an adequate supply of nutrients to smooth muscle cells throughout the cartilage tissue construct by convection.

Tissue Culture Vessels

Those of ordinary skill in the art will readily appreciate that the cell culture and bioengineering methodologies described herein may be carried out in a variety of environments (i.e., vessels or containers). Smooth muscle cells are anchorage dependent, and therefore to grow in culture these cells require a nontoxic, biologically inert, and optically transparent surface that will allow cells to attach and allow movement for growth. Tissue culture vessels or plates include specially-treated polystyrene plastic that are supplied sterile and are disposable. These include Petri dishes, multi-well plates, microtiter plates, roller bottles, screwcap flasks (T-25, T-75, T-150 $cm^2$ of surface area), culture bags or any container capable of holding cells, preferably in a sterile environment.

In one embodiment of the present invention, a bioreactor is also useful for bioengineering sphincters and culturing smooth muscle cells. For example, several manufacturers currently make devices that can be used to grow cells and be used in combination with the methods of the present invention. See for example, Celdyne Corp., Houston, Tex.; Unisyn Technologies, Hopkinton, Mass.; Synthecon, Inc. Houston, Tex.; Aastrom Biosciences, Inc. Ann Arbor, Mich.; Wave Biotech LLC, Bedminster, N.J. Further, patents covering such bioreactors include U.S. Pat. Nos. 6,096,532; 6,001,642, 5,985,653; 5,888,807; 5,688,687, 5,605,835, 5,190,878, which are incorporated herein by reference.

There are a number of different kinds of bioreactors, devices designed to provide a low-shear, high nutrient perfusion environment, available on the market. For example, the invention may be carried out in a rotating wall bioreactor, which consists of a small inner cylinder, the substrate for the electrospinning process, positioned inside a larger outer cylinder. Although the electrospun matrix can be fabricated on the inner cylinder, other locations within the bioreactor also may be used for placement of the matrix for seeding. The gap between the inner and outer cylinders serves as the culture vessel space for cells. Culture medium is oxygenated via an external hydrophobic membrane. The low shear environment of the rotating bioreactor promotes cell-cell and cell-extracellular matrix (ECM) interactions without the damage or "washing away" of nutrients that occurs with active stirring.

Matrix Materials

To generate the bioengineered sphincters of the present invention, a homogenous smooth muscle cell population is grown in a cell culture vessel containing one or more extracellular matix proteins. In one embodiment, the smooth muscle cells are grown in fibrin gel to produce a transient three-dimensional matrix well suited to the development of contractile tissues. Fibrin gels are formed by the enzymatic cleavage of fibrinogen by the serine proteinase thrombin allowing the fibrin monomers to interact and form fibrils. Within a fibrin matrix, cells rapidly migrate, proliferate, and digest the fibrin replacing it with their own extracellular matrix (ECM). Grassl et al., *Journal of Biomedical Material Research* 60: 607-612, 2002. Grassl et al., *Journal of Biomedical Materials Research* 66A: 550-561, 2003. Neidert et al., *Biomaterials* 17: 3717-3731, 2002. Ross & Tranquillo *Matrix Biology* 22: 477-490, 2003).

Matrix proteins, such as fibrin, guide smooth muscle cells to form a ring around the cylindrical mold in culture to form the functional sphincter. The type of matrix that may coat the cylindrical ring and cell culture vessel of the invention is virtually limitless and may include both biological and synthetic matrices. The matrix will have all the features commonly associated with being "biocompatible," in that it is in a form that does not produce an adverse, allergic or other untoward reaction when administered to a mammalian host. Such matrices may be formed from either natural or synthetic materials.

It is contemplated that the bioengineered sphincter may serve as a replacement organ and may be inserted in vivo to treat mammals exhibiting sphincter dysfunction. For insertion of the sphincter into a mammal in need, the matrices may be fabricated from biodegradable materials that will erode over time in the body to yield a completely natural tissue. These matrices will not induce any chronic inflammatory responses, and cannot serve as a long-term site for infection. Biodegradable polymers have been utilized to engineer tissues that will be structurally integrated with the host tissue. In addition, the use of synthetic, biodegradable matrices will often be advantageous as the degradation time of such synthetic matrices can be designed to coincide with the formation of a new tissue from the cultured cells.

It will of course be understood that biodegradable matrices for use in the invention are not confined to being synthetic matrices. A number of naturally-derived matrix-like materials may be used that will eventually biodegrade in an in vivo environment. Thus, in the context of the present invention, the term biodegradable is not necessarily synonymous with synthetic matrices.

The choice of matrix material will differ according to the particular circumstances and the type of smooth muscle cells used or the type of sphincter to be bioengineered. Physical and chemical characteristics, such as, e.g., biocompatibility, biodegradability, strength, rigidity, interface properties and even cosmetic appearance, may be considered in choosing a matrix, as is well known to those of skill in the art. Appropriate matrices will act as an in situ scaffolding through which mammalian repair cells may migrate.

Possible non-biodegradable matrices include non-biodegradable polymers such as semipermeable polymers such as poly(acrylonitrile-co-vinyl chloride), polylysine, cellulose acetate and polysulfone. Although generally intended for use in immobilized cells, the use of such polymers in the context of the present invention is certainly not excluded. These polymers may also be used with a variety of gels, including alginate and polyphosphazenes.

Polyphosphazenes are synthetic polymers, and aqueous solutions of polyphosphazenes will gel in the presence of specific ions. These polymers can be used in the same manner as alginate. The exceedingly stable backbone of these synthetic polymers allows significant alterations in side-group functionality without losing the gentle, physiologic gelling conditions.

There are advantages and disadvantages of both natural materials, e.g., collagens, and synthetic materials, e.g., polyglycolic acids. Synthetic materials that incorporate design concepts or specific biological activities of natural biomaterials may combine the advantages of both types of materials. The reproducible, large-scale synthesis and flexible properties of synthetic polymers can be combined with the biocompatibility and biological activity of natural materials. Such materials may be used in this invention.

Amino acid sequences in ECM molecules that are responsible for specific biological activities, e.g., cell binding, have been identified in recent years. This information allows researchers to design synthetic materials that are capable of precise cellular interactions. Genetic engineering approaches are being utilized to prepare artificial proteins with a desired backbone structure and amino acid side chains that promote cell adhesion. These artificial proteins can be expressed in bacterial cells, isolated and purified, and utilized to form matrices or coat other surfaces. This approach offers tremendous control over both the properties (bulk and surface) of the material, and its ability to interact with cells.

Traditional synthetic routes are also being used to develop biodegradable polymers that contain cell recognition peptides as side chains. The advantages of synthetic polymers, such as polylactide, can be combined with the specific biological activity of ECM molecules with this approach. A similar approach is the synthesis of short amino acid chains containing a desired functional group that can be covalently bonded or adsorbed onto matrices fabricated from other synthetic materials. Such biomimetic synthetic polymers and cell-adhesion peptides are proposed for use as implants for tissue regeneration and transplantation. These and any of the foregoing or other "second generation" matrices may be used in the context of the present invention.

Exogenous Factors

Histology revealed the bioengineered sphincters were composed of cells surrounded by pieces of undigested fibrin matrix. To address this issue, growth factors may be added to increase ECM production by the smooth muscle cells. For example, TGFβ has previously been shown to increase the amount of ECM in fibrin-based engineered tissues (Ross & Tranquillo, *Matrix Biology* 22: 477-490, 2003). Incorporating TGFβ into the cell culture system of the present invention would therefore increase ECM production and cell differentiation, resulting in a less compliant ring with enhanced force production and transmission. Furthermore, altering how the cells are seeded by mixing the cells directly with fibrin rather than atop the polymerized gel, may increase homogeneity of the bioengineered sphincter and reduce the percentage of undigested fibrin comprising the sphincter.

If desired, protein growth factors that affect the proliferation of smooth muscle cells may be used in conjunction with the bioengineering processes of the present invention. Likewise, cells that naturally elaborate such factors and/or recombinant cells engineered to produce and secrete such factors may also be used to further stimulate the proliferation of cells and tissues, or to direct the development of a given tissue over another tissue when using starter cells that have the natural capacity to regenerate smooth muscle cells and tissues.

The microenvironment of an engineered tissue following transplantation may also be regulated during the process of tissue development, and perhaps beyond this time. Specific ECM molecules, growth factors, mechanical signals and/or mass transport conditions may be required to ensure optimal development of bioengineered sphincter with appropriate structure and function following application of sphincter or smooth muscle tissue to the site of implantation.

Synthetic materials that incorporate specific peptides to enhance cell adhesion may be used for organ replacement, including those that incorporate a variety of different peptides in order to mimic the multi-functional nature of ECM molecules. For organ replacement, growth factors or cytokines for promoting tissue development may be lacking or deficient in the host tissue site that the engineered tissue is applied to. To address this concern, traditional controlled drug delivery technology may be integrated with the bioengineered sphincter tissue to provide transplanted smooth muscle cells with specific growth factors in their local environment.

Other cytokines and agents that may be added to the ECM include ascorbic acid, nonessential amino acids, PDGF (platelet derived growth factor); bFGF (basic fibroblast growth factor): IGF-1 (insulin-like growth factor 1); EGF (epidermal growth factor); and VEGF. Some of these cytokines are available commercially, could be produced commercially, or can be extracted from harvested platelets (platelet releasates). The effects of a given cytokine upon tissue physiology can include one or more of the following: smooth muscle and fibroblast mitogenic effects (induces division and growth of cells); stimulation of the release of cytokines from other cells; chemoattractant (bringing new healing cells into local region); and angiogenesis (development of new blood vessels).

Mechanical signals are known to regulate the development of a variety of tissues, including muscle. For example, engineered tendons that are not subjected to mechanical loading do not develop mechanical moduli as high as normal tendons, even though they appear to be histologically identical. Mechanical stimuli (e.g., strain, shear) also clearly regulate the gene expression of cultured cells. To engineer an optimally functional sphincter tissue it may be necessary to provide the correct mechanical stimuli during the process of tissue development.

It will be understood that the exogenous factors for use herewith may be produced by a population of cells that is co-cultured with the smooth muscle cells and/or that is administered to the smooth muscle tissue of an animal with the tissue sample or matrix-tissue sample. Examples of cells that may be co-cultured with smooth muscle cells to generated the bioengineered sphincters of the invention include embryonic nerve cells and stem cells. The use of natural smooth muscle cells that elaborate any of the aforementioned or other growth factors, hormones or cytokines is thus contemplated. Such cells may be autologous cells that have also been proliferating in culture ex vivo.

Equally, recombinant cells engineered to produce the growth factors, hormones, cytokines, hormone, neurotransmitters and the like may also be employed and co-cultured with smooth muscle cells to generate the bioengineered sphincters of the present invention. Recombinant engineering for protein production and secretion, generally using recombinant vectors, is routine in the art. Examples of useful host cell lines that may so engineered include, for example, VERO cells, HeLa cells, Chinese hamster ovary (CHO) cell lines, and W138, BHK, COS-7, 293 and MDCK cell lines.

Expression vectors for such cells ordinarily include (if necessary) an origin of replication, a promoter located in front of the gene to be expressed, along with any necessary ribosome binding sites, RNA splice sites, polyadenylation site, and transcriptional terminator sequences. For use in mammalian cells, the control functions on the expression vectors are often obtained from viral material. For example, commonly used promoters are derived from polyoma, Adenovirus 2, and frequently, from Simian Virus 40 (SV40). The early and late promoters of SV40 virus are particularly useful because both are obtained easily from the virus as a fragment which also contains the SV40 viral origin of replication. It is also possible to utilize promoter or control sequences normally associated with the desired gene sequence, provided such control sequences are compatible with the host cell systems.

In mammalian cell vector systems, the origin of replication may be obtained from either construction of the vector to include an exogenous origin, such as may be derived from SV40 or other viral (e.g., Polyoma, Adeno, VSV, BPV) source, or may be obtained from the host cell chromosomal replication mechanism. If the vector is integrated into the host cell chromosome, the latter is often sufficient.

Uses of the Three-Dimensional Culture System

The three-dimensional culture system of the invention can be used in a variety of applications. These include, but are not limited to, transplantation or implantation of either the bioengineered sphincter or the smooth muscle cells in vivo; screening the effectiveness and cytotoxicity of compounds, allergens, growth/regulatory factors, and pharmaceutical compounds, in vitro; elucidating the mechanism of smooth muscle cell contraction and relaxation; studying the mechanism by which drugs and/or growth factors operate to effect smooth muscle cell function, contraction and relaxation.

The growth of fully functional sphincters comprising contracting smooth muscle cells in culture may be a method for better understanding the function of smooth muscle cells and sphincters which is useful for identifying agents that modulate smooth muscle cell contraction, relaxation and cell function. Three-dimensional bioengineered sphincters or smooth muscle implants may, according to the invention, be used to replace or augment existing tissue or to introduce new or altered tissue.

The three-dimensional cultures may be used in vitro to screen a wide variety of compounds or test agents for effectiveness and cytotoxicity of modulators of smooth muscle cell contraction, pharmaceutical agents and growth/regulatory factors such as endothelins, GABA receptor modulators and cannaboids, to name a few. The bioengineered sphincters are maintained in vitro and exposed to the compound or agent to be tested. The activity of a cytotoxic compound can be measured by its ability to damage or kill cells in culture. This activity may readily be assessed by vital staining techniques. The effect of a test agent on cell growth may be assessed by measuring cell proliferation. The effect of a compound or agent on smooth muscle cell contraction or relaxation is assessed by determining the change in peak isometric contractions using standard techniques such those method described in detail in Example 3. The proliferation and apoptotic rates of the cells may be analyzing using standard cytological and/or histological techniques including the use of immunocytochemical techniques employing antibodies that define type-specific cellular antigens. The effect of various drugs on normal cells cultured in the three-dimensional system may be assessed.

The three-dimensional cultures of the invention may be used as model systems for the study of physiologic or pathologic conditions. For example, the three-dimensional sphincters may be used to determine the limits of cell growth and mechanical signal transduction. In addition, the chemical and physical stress on the smooth muscle that mimic smooth muscle hypertrophy observed in response to both physiological and pathological stimuli may be studied. These experiments provide a better understanding of the mechanisms involved in pathogenesis of sphincter and smooth muscle dysfunction.

Test agents of the present invention can be any organic or inorganic molecule, complex or substance. Exemplary test agents are obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (*Anticancer Drug Des.*, 12:145, 1997). Numerous chemical libraries already exist, e.g., as proprietary libraries of pharmaceutical companies, and compounds in such libraries are suitable test agents. Test agents of the invention include fusion proteins, polypeptides, peptidomimetics, prodrugs, receptors, binding agents, ribozymes, small molecules, peptides, antibodies, or other drugs which can be screened for the ability to modulate smooth muscle cell contraction and relaxation.

Organ Replacements

For organs replacement, such as replacement of a dysfunctional sphincter, it is contemplated that a biodegradable matrix will likely be most useful. A biodegradable matrix is generally defined as one that is capable of being reabsorbed into the body. Potential biodegradable matrices for use in connection with the compositions, devices and methods of this invention include, for example, biodegradable and chemically defined calcium sulfate, tricalciumphosphate, hydroxyapatite, polyactic acid, polyanhidrides, matrices of purified proteins, and semipurified extracellular matrix compositions.

Other biocompatible biodegradable polymers that may be used are well known in the art and include, by way of example and not limitation, polyesters such as polyglycolides, polylactides and polylactic polyglycolic acid copolymers ("PLGA")(Langer & Folkman, *Nature* 263:797-8001976); polyethers such as polycaprolactone ("PCL"); polyanhydrides; polyalkyl cyanoacrylates such as n-butyl cyanoacrylate and isopropyl cyanoacrylate; polyacrylamides; poly(orthoesters); polyphosphazenes; polypeptides; polyurethanes; and mixtures of such polymers.

In one aspect, the biocompatible biodegradable polymer is a copolymer of glycolic acid and lactic acid ("PLGA") having a proportion between the lactic acid/glycolic acid units ranging from about 100/0 to about 25/75. The average molecular weight ("MW") of the polymer will typically range from about 6,000 to 700,000 and preferably from about 30,000 to 120,000, as determined by gel-permeation chromatography using commercially available polystyrene of standard molecular weight, and have an intrinsic viscosity ranging from 0.5 to 10.5.

Another type of biomaterial that may be used is small intestinal submucosa (SIS). The SIS graft material may be prepared from a segment of jejunum of adult pigs. Isolation of tissue samples may be carried out using routine tissue culture techniques such as those described in Badybak et al., (*J. Surg. Res.* 47:74-80, 1989). SIS material is prepared by removal of mesenteric tissue, inversion of the segment, followed by removal of the mucosa and superficial submucosa by a mechanical abrasion technique. After returning the segment to its original orientation, the serosa and muscle layers are rinsed and stored for further use.

Fibrin gel is a suitable material that may be used for organ replacement. Fibrin gel is a network made up of monomeric fibrin molecules generated by activation of fibrinogen by thrombin. This biopolymer is known to be involved in hemostatis and wound healing. Fibrin is a biodegradable material that has been used for temporary tissue replacement and as an absorbable implant material.

Another particular example of a suitable material is fibrous collagen, which may be lyophilized following extraction and partial purification from tissue and then sterilized. Matrices may also be prepared from tendon or dermal collagen as may be obtained from a variety of commercial sources, such as, e.g., Sigma and Collagen Corporation.

In addition, lattices made of collagen and glycosaminoglycan (GAG) such as that described in Yannas & Burke, U.S. Pat. No. 4,505,266, may be used in the practice of the invention. The collagen/GAG matrix may effectively serve as a support or "scaffolding" structure into which repair cells may migrate.

The various collagenous materials may also be in the form of mineralized collagen. For example, the fibrous collagen implant material termed UltraFiber.™., as may be obtained from Norian Corp., (1025 Terra Bella Ave., Mountain View, Calif., 94043) may be used for formation of matrices. U.S. Pat. No. 5,231,169, incorporated herein by reference, describes the preparation of mineralized collagen through the formation of calcium phosphate mineral under mild agitation in situ in the presence of dispersed collagen fibrils.

At least 20 different forms of collagen have been identified and each of these collagens may be used in the practice of the invention. For example, collagen may be purified from hyaline cartilage, as isolated from diarthrodial joints or growth plates. Type II collagen purified from hyaline cartilage is commercially available and may be purchased from, e.g., Sigma Chemical Company, St. Louis. Type I collagen from rat tail tendon may be purchased from, e.g., Collagen Corporation. Any form of recombinant collagen may also be employed, as may be obtained from a collagen-expressing recombinant host cell, including bacterial yeast, mammalian, and insect cells. When using collagen as a matrix material it may be advantageous to remove what is referred to as the "telopeptide" which is located at the end of the collagen molecule and known to induce an inflammatory response.

Assays for Measuring Smooth Muscle Cell Function

The standard protocols for defining and testing gastrointestinal smooth muscle strips (contraction, relaxation, and spontaneous tone) in vivo are taught in Glavind et al., Am. J. of Physiol. 265: G792-G798, 1993, Glavind et al., Glavind et al., American Journal of Physiology 272: G1075-G1082, 1997, Chakder & Rattan, *Am J. Physiol* 264: G702-G707, 1993, Knudsen et al., *Amer. J. of Physiol.* 269: G232-G239, 1995. Following stretch of the muscle strip and a period of equilibrium, spontaneous tension/tone has been described as either steady tension oscillations or stable tension/tone for an extended period of time if undisturbed, accompanied by the ability to contract and relax with the appropriate stimulation. The bioengineered sphincters of the invention (described in Example 2) displayed spontaneous tension. Following stretch and stabilization of the baseline tension, bioengineered rings exhibited steady and stable tension/tone over a period of time, and change in the baseline tension was only due to agonist-induced stimuli. The stable tension generated by the rings arbitrarily set to zero for the purposes of consistent force measurements.

These methods may be used for bioengineered sphincters generated using any circular smooth muscle cells and may be used to determine if the bioengineered sphincter are functionally similar to any naturally occurring mammalian sphincter or isolated smooth muscle cell. The experimental design of the bioengineered sphincters is as follows: 1) The bioengineered sphincter ring generates a spontaneous basal tone. 2) Upon addition of the relaxant transmitter 8-br-AMP, 8-br-cAMP, the bioengineered sphincter induces a rapid and significant decrease in the basal tension/basal tone (relaxation) that is measured and expressed as decrease in force generation in $\mu N$. 3). Upon addition of acetylcholine, acetylcholine induced a great and immediate generation of force measured (contraction) in $\mu N$. 4) Addition of 8-br-cAMP-induced rapid relaxation of acetylcholine-induced contraction and force generation of bioengineered rings. Data analysis on the bioengineered sphincters described in Example 2, revealed consistent and reproducible results in response to these agonists.

In addition, smooth muscle cell function may be measured in vascular muscles as described in Gorenne et al., *Amer. J. Physiol.* 5:H131-H138, 1998. For measurement of isometric force, arteries may be cleaned of excess connective tissue, and the endothelium is removed by gently scraping the intima with a cotton swab. Medial strips of swine carotid artery (0.5 3 7 mm) are mounted on a Muscle Research Station at room temperature and allowed to equilibrate in PSS for 90 minutes. A passive force of 100 mg is applied to all tissues. After equilibration, tissues are maximally contracted with agonists (50 $\mu M$) and then washed in PSS until basal force is recovered. The tissues are then incubated for 2 hours in either PSS or PSS containing an antagonist. After this incubation period, cumulative concentration-response curves to agonists are performed.

Disease States Relating to Sphincter Malfunction

Fecal incontinence is associated with reduced anal closure pressure and mechanical stress maintaining tissue coaptation and closure of the anal canal, resulting in the inability to control the passage of gas or stools (feces) through the anus (Delechenaut et al., *Dis Colon Rectum* 35: 847-849, 1992; Sun et al., *Gastroenterology* 97: 130-135, 1989). This is largely attributed to decreased mechanical efficiency of the internal anal sphincter (IAS) (Jones et al., *Can J Physiol Pharmacol* 16: 249-257, 2002; Laurberg et al,. *Dis Colon Rectum* 32: 737-742, 1989; Sultan et al., *British Medical Journal* 308: 887-891, 1994). Epidemiological studies have shown that fecal incontinence affects 2-15% of the population Rossman et al., *Dig Dis Sci* 38: 1569-1580, 1993; Nelson et al., *JAMA* 274: 559-561, 1995. *Gut* 50: 480-484, 2002, Perry et al., *Gut* 50: 480-484, 2002, Talley et al., *Gastroenterology* 102: 895-901, 1992), including people of all ages and social backgrounds, thus making it one of the most common gastrointestinal disorders. A diagnosis of fecal incontinence often leads to devastating social, psychological, and economic consequences as well as a significantly lower quality of life (Perry et al. *Gut* 50: 480-484, 2002).

Urinary incontinence, such as stress incontinence, may be caused by weakening of the urinary sphincter that controls the flow of urine from the urinary bladder. The urinary sphincter may weaken as a consequence of prostate surgery or pelvic surgery, multiple pregnancies, vaginal births or a prolapsed pelvis. The weakening of the urinary sphincter may be a symptom of a nervous system disorder such as Parkinson's disease or multiple sclerosis. The weakening of the urinary sphincter may be the symptom of other disorders such as diabetes or chronic coughing caused by lung disorders such as chronic bronchitis and asthma. In addition, weakening of the smooth muscle cell contraction in the urethra also contributes to urinary incontinence. Urinary incontinence is a social and hygienic problem that is known to affect about 50% of all women occasionally and nearly 20% of women over the age of 75 experience daily urinary incontinence.

Gastroesophageal reflux disease (GERD) is caused by the weakening of the cardiac sphincter or the lower esophageal sphincter (LES). GERD is a common disorder caused most commonly by frequent transient relaxations of the lower esophageal sphincter (LES). If the lower esophageal sphincter fails to function properly, stomach contents, including acid, enzymes, and bile may flow backwards into the esophagus, causing heartburn or other disease symptoms, damage to the esophagus, and the development of precancerous lesions.

Stenosis or dyskinesia of the sphincter of Oddi, also known as biliary dyskinesia, is a structural or functional abnormality of the sphincter of Oddi that interferes with bile drainage. Sphincter of Oddi dysfunction is a common postcholecysteectomy (surgical removal of the gall bladder) complication. After gall surgery, denervation sensitivity of the sphincter of Oddi after surgery results in abnormalities of the sequencing or frequency rates of the sphincteric contractions. Current treatments for dyskinesia of the sphincter of Oddi include treatment with pharmaceuticals to induce relaxation of the sphincter and sphincterotomy. The methods of the present invention may identify agents that inhibit smooth muscle contraction or induce relaxation of smooth muscle, which may be treatments for stenosis or dyskinesia of the sphincter of Oddi.

In these disorders, inadequate barrier function can be the result of either a mechanical defect in the sphincter, a low resting pressure in the sphincter, an overly compliant sphincter, abnormal afferent nerve impulses that trigger transient sphincter relaxations, or improper sensing of and control of lumenal contents.

HSP27 and Smooth Muscle Contraction

Protein-protein interactions are fundamental to all biological processes, including smooth muscle contraction, and explicit folding of proteins is essential for proper function. Aging is accompanied by defects in protein-protein interaction, protein turnover and protein folding. Protein turnover is greatly decreased with age (Ryazanov & Nefsky, *Mechanisms of Ageing and Development* 123 (2-3): 207-213, 2002), resulting in less protein available for normal turnover. Aged individuals show an increased incidence of post-translational errors which result in folding defects and subsequent defects in protein oxidation (Stadtman &Berlett, *Drug Met. Rev.* 30(2): 225-243, 1998; Dukan et al., *Proc. Natl. Acad.* 97(11): 5746-5749, 2000). Signaling networks may lose their original stringency due to the synthesis of damaged proteins and improper protein folding resulting in irregular protein phosphorylation (Soti and Csermely, *Exp. Gerontology,* 38(10): 1037-1040, 2003).

Chaperone proteins, such as HSP27, normally govern the folding process by interacting with unfolded proteins and preventing their aggregation. Damaged and misfolded proteins bind to chaperones liberating the heat shock factors (HSF) from the chaperone complex. Out of the chaperone complex, HSF is active and initiates the transcription of chaperone genes (Morimoto, *Cell,* 110(3): 281-284, 2002). Passive chaperone function of whole cell lysates is decreased in aged rats compared to those of their younger counterparts (Nardai et al., Exp. Gerontology 37(10-11): 1257-1262, 2002). This may result in a decrease in chaperones or chaperone overload. Chaperone overload occurs when there is a shift in the balance between misfolded proteins and available free chaperones in aging organisms (Soti and Csermely, *Exp. Gerontology,* 38 (10): 1037-1040, 2003). The accumulation of chaperone substrates along with an impaired chaperone function may exceed the folding capacity of specific chaperone targets and lead to deterioration of cell function. It has previously been shown that inhibition of ceramide-induced activation of MAP kinase in aged rats result in decreased phosphorylation of HSP27 and decreased cellular contraction (Bitar et al., *Amer. J. Physiol.* 284: G1-G7, 2003). Studies into the mechanism of age-dependent muscle dysfunction have demonstrated differences in the content of heat shock proteins (HSP) in adult verses aged muscle tissue (Bitar, *Amer. J. Physiol.* 284: G1-G7, 2003; Soti & Csermely, *Exp. Gerontology* 38(10): 1037-1040, 2003). For example, skeletal muscle of adult mice show an increase of HSP content following exercise, whereas aged mice do not.

In colonic smooth muscle, HSP27 has been implicated to participate in PKC-mediated smooth muscle contraction (Bitar et al., *Amer. J. Physiol.* 284: GI-G7, 2003; Bitar et al., *Amer. J. Physiol.* 282 (5): G894-903, 2002; Lavoie et al., *Mol. Cell. Biol.* 15(1): 505-516,1995; Schafer et al., *Amer. J. Physiol.* 277 (6 Pt. 1): C1032-1043, 1999). Studies on colonic smooth muscle has shown that HSP27 phosphorylation modulates myosin association with actin and appears to be necessary for reorganization of HSP27 inside the cell directly correlated with the PKC signal transduction pathway (Bitar et al., *Amer. J. Physiol.* 282 (5): G894-903, 2002). Interaction of actin with myosin is regulated by association of contractile proteins at different levels. In colonic smooth muscle, HSP27 phosphorylation has been found to effect the association of tropomyosin with HSP27 (Somara et al, *Amer. J. Physiol.* 286(6): C1290-1301, 2004) and has also been found to be crucial for maintaining the association of PKCA with RhoA in the membrane (Patil et al., *Amer. J. Physiol.* 286: G635-G644, 2004). Studies in colonic smooth muscle cells show that phosphorylated HSP27 is not only essential for association of contractile proteins and signal transduction but also for contraction. Colonic smooth muscle transfected with non-phosphomimic HSP27 showed 75% inhibition of contraction suggesting the crucial role of phosphorylated HSP27 in contraction of smooth muscle (Patil et al, *Amer. J. Physiol.* 286: G635-G644, 2004). Colonic smooth muscle cells from the aged rats have shown decreased contraction along with decreased association of actin with myosin and decreased association of tropomyosin with HSP27, which can be ascribed to decreased phosphorylation of HSP27 (Bitar, *Amer. J. Physiol.* 284: G1-G7, 2003).

As described in detail in Example 4, phospho-HSP27 reinstated contractile response in bioengineered internal anal sphincter (IAS) rings that comprise smooth muscle cells from aged rats. Thus, phosphorylated HSP27 may be a therapeutic for reinstating the contractile force in sphincters that dysfunction or weaken with increasing age. The experiments described herein demonstrate that phospho-HSP27 may reverse the aging process in smooth muscle cells. Therefore, the invention contemplates methods of treating age-related disorders associated with sphincter dysfunction and sphincter contractile weakening comprising administering phospho-HSP27 or a pharmaceutical composition comprising phospho-HSP27 in an amount effective to induce or regenerate smooth muscle contraction to a mammal in need.

Pharmaceutical Compositions

An aspect of the invention involves administering agents to mammals in need, e.g., administering an agent to a mammal for modulating smooth muscle cell or sphincter function. In preferred variations of the invention, the agent is formulated with a pharmaceutically acceptable or a physiological acceptable carrier for administration.

Also, the present invention pertains to pharmaceutical compositions comprising an agent identified by the methods of the invention such as phospho-HSP27. The agent can be formulated with a pharmaceutically acceptable or physiologically acceptable carrier or excipient to prepare a pharmaceutical composition. The carrier and composition can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active agents.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose and magnesium carbonate.

Methods of introduction of these compositions include, but are not limited to, intradermal, intramuscular, intraperitoneal, intraocular, intravenous, subcutaneous, topical, oral and intranasal. Other suitable methods of introduction can also include gene therapy (as described below), rechargeable or biodegradable devices, particle acceleration devises ("gene guns") and slow release polymeric devices. The pharmaceutical compositions of this invention can also be administered as part of a combinatorial therapy with other agents.

The composition can be formulated in accordance with the routine procedures as a pharmaceutical composition adapted for administration to human beings. For example, compositions for intravenous administration typically are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

For topical application, nonsprayable forms, viscous to semi-solid or solid forms comprising a carrier compatible with topical application and having a dynamic viscosity preferably greater than water, can be employed. Suitable formulations include but are not limited to solutions, suspensions, emulsions, creams, ointments, powders, enemas, lotions, sols, liniments, salves, aerosols, etc., which are, if desired, sterilized or mixed with auxiliary agents, e.g., preservatives, stabilizers, wetting agents, buffers or salts for influencing osmotic pressure, etc. The agent may be incorporated into a cosmetic formulation. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., pressurized air.

Agents can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine and procaine.

The agents are administered in a therapeutically effective amount. The amount of agents which will be therapeutically effective in the treatment of a particular disorder or condition, such as fecal incontinence, gastroesophageal reflux disease, urinary incontinence and biliary dyskinesia, will depend on the nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the symptoms of schizophrenia, and should be decided according to the judgment of a practitioner and each patient's circumstances. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use of sale for human administration. The pack or kit can be labeled with information regarding mode of administration, sequence of drug administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a single vial or tablet. Agents assembled in a blister pack or other dispensing means is preferred. For the purpose of this invention, unit dosage is intended to mean a dosage that is dependent on the individual pharmacodynamics of each agent and administered in FDA approved dosages in standard time courses.

The following examples are for illustration purposes only, and should not be construed as limiting the scope of the invention in any way. Example 1 describes the isolation of rabbit internal anal sphincter cells and determination of contractibility of these cells. Example 2 describes the generation of a three-dimensional bioengineered sphincter. Example 3 describes agonist-induced contraction and relaxation of the bioengineered sphincter. Example 4 demonstrates that heat shock protein 27 (HSP27) regeneration of smooth muscle cell contractile force. Example 5 describes the development of three-dimensional physiological models of smooth muscle tissue.

EXAMPLES

Example 1

Isolation of Internal Anal Sphincter Cells and Determination of Contractility

Smooth muscle cells were isolated from the internal anal sphincter (IAS) of New Zealand White rabbits as described previously (Bitar et al., *Am J Physiol* 260: G537-G542, 1991; Bitar et al., *Am J Physiol* 242: G400-G407, 1982). Briefly, the IAS, consisting of the most distal 3 mm of the circular muscle layer, ending at the junction of skin and mucosa, was removed by sharp dissection. The sphincter was rapidly cleaned and striped of connective tissue in ice cold carbonated Krebs solution containing 2% penicillin-streptomycin. The tissue was cut into small pieces and transferred to a 100 mm plate containing 15 ml of HEPES buffer (pH 7.4; NaCl (115 mM), KCl (5.7 mM), $KH_2PO_4$ (2.0 mM), HEPES (24.6 mM), $CaCl_2$ (1.9 mM), $MgCl_2$ (0.6 mM), glucose (5.6 mM), 0.01% soybean trypsin inhibitor, and 0.184 (wt/vol) DMEM) with 0.1% collagenase type II (Worthington Biochemical Corp., Lakewood, N.J.) for digestion in an incubator (37° C. with 5% $CO_2$) for 1 hour. Fresh HEPES buffer (15 ml) with collagenase was added and the contents of the plate were mechanically dissociated using a 10 ml pipette and incubated for 1 additional hour. After the second digestion period, the cells were collected, centrifuged at 800×g for 10 minutes and the supernatant discarded. The cells were washed (3×) a to ensure removal of excess collagenase and ultimately re-suspended in either HEPES buffer or 0 $Ca^{2+}$/2 mM EGTA HEPES buffer (HEPES without $CaCl_2$ and containing 2 mM EGTA).

To determine the effect of acetylcholine on contraction of isolated muscle cells, acetylcholine ($10^{-7}$ M) was added to a suspension of isolated smooth muscle cells for 30 seconds or 4 minutes with untreated cells as controls. The reaction was stopped and cells were fixed by the addition of 0.1 ml of acrolein at a final concentration of 0.1%. Individual cell lengths were measured by computerized image micrometry (Bitar et al., *Am J Physiol* 242: G400-G407, 1982. Bitar et al., *Science* 216: 531-533, 1982). The length of cells in the control state or after addition of acetylcholine was obtained by measuring 30-50 cells encountered randomly in successive microscopic fields from each of three separate experiments. The contractile response is defined as the decrease in the average length of the cells counted and is expressed as the percent change from the control length.

Acetylcholine-induced stimulation of isolated smooth muscle cells from the rabbit IAS resulted in a sustained contractile response. Contraction of the treated IAS cells compared to control was 28.85±3.20% at 30 seconds and was sustained for 4 minutes 27.09±4.43% (n=3). To determine the calcium dependence of this response, parallel experiments were performed in 0 $Ca^{2+}$/2 mM EGTA HEPES Buffer. As expected, acetylcholine-induced stimulation of isolated smooth muscle cells resulted in minimal contractile response in the absence of $Ca^{2+}$, (0.5±4.47% and 4±3.91% decrease in cell length at 30 seconds and 4 minutes, respectively). These data are similar to previously published contractile response of isolated smooth muscle cells to bombesin and to exogenous PKC. Bitar et al., *Life Sci* 47: 2429-2434, 1990; Bitar et al, *Am J Physiol* 260: G537-G542, 1991).

Example 2

Bioengineering a Three-Dimensional Sphincter Ring

Culture plates (35 mm) were prepared as described previously (Dennis et al., *In Vitro Cellular & Developmental Biology Animal* 36: 327-335, 2000). Briefly, 1.5 ml of the polymer SYLGARD™ (polydimethylsiloxane—PDMS) was poured into each plate and allowed to cure for 24 hours. The polymer layer provided an anchor that materials could be easily pinned in place and provided a surface to which, unless coated, the cells could not adhere. A 5 mm diameter cylindrical SYLGARD mold was placed in the center of the dish to provide a luminal space for the engineered sphincter (FIG. 1, Panel A). Adhesion of the mold to the SYLGARD coated culture dish was facilitated by pressing the mold firmly against the bottom of the dish with forceps. The culture dish was sterilized with 70% ethanol for 30 minutes. Ethanol was then aspirated and culture dishes were exposed to UV light for 1 hour. Subsequently, growth media (500 µl)

containing 10 U/ml thrombin was added to each dish and the dishes were agitated until the bottom of the dish was entirely coated with media. Finally, 200 µl of 20 mg/ml fibrinogen was added to each plate and gently swirled. The fibrin polymerized approximately 15 minutes later and the dishes were ready for cell seeding.

Primary cells isolated from rabbit IAS were expanded in 75 cm$^2$ flasks for approximately 1 week. The cells were then detached with trypsin-EDTA and $5^4$, $7.5^4$, or $10^4$ cells/ml and were added to the plates in a final volume of 2 ml. Five to seven days after plating (depending on the density of the cells) growth medica (Dulbecco's Modified Eagle Medium (Gibco™, catalog #12430-054), with 15% FBS, 3% penicillin-streptomycin, and 0.6% L-glutamine) was replaced with differentiation media (73% DMEM (Gibco™, catalog #12430-054), 20% Media 199, 7% heat-inactivated horse serum, and 1% penicillin-streptomycin), to promote the formation of adult cellular connections and smooth muscle differentiation, and returned to the incubator. The differentiation media was replaced every 2-3 days until the ring was fully contracted and ready for testing. IAS rings were fully formed in approximately 10 days; however, time spent in culture for each construct varied depending on the number of cells plated and the experimental design designated for each construct.

As the cells became confluent, they began to digest and contract the fibrin gel toward the center of the culture dish. As shown in FIG. 1 (Panels B-E), five to ten days after seeding on fibrin, the cells contracted the gel into a cylindrical ring around the SYLGARD mold in the center of the dish. The rate of gel contraction was dependent on the number of cells initially plated, as constructs seeded with 100,000 cells consistently formed rings faster than constructs seeded with 50,000 cells. During the formation of this cylindrical ring structure, the muscle cells reorganized along the line of force until they formed a parallel array of cells. The cells appeared to proliferate within the fibrin gel only until they reached confluence, regardless of seeding density. This result suggested that normal density-dependent contact inhibition of cell division (Blankn et al., *J Cell Biol* 107: 299-306, 1988) had occurred during the formation of IAS rings. The resulting three-dimensional IAS rings remained stable in culture for up to 40 days.

For histological analysis under a light microscopy, the bioengineered IAS rings were fixed in 4% paraformaldehyde. The rings were processed and embedded in paraffin wax according to standard histological procedures (Carson, *Histotechnology: A Self-Instructional Text*. Chicago: American Society for Clinical Pathology Press, 1997). All sections were made (5-8 µm thick) using a rotary microtome. Staining of the histological sections was performed to view general structure using Harris's Hematoxylin and Eosin (Humason, *Animal Tissue Techniques*. Baltimore: Johns Hopkins University Press, 1997).

Histological analysis of the bioengineered IAS rings revealed one uniform cell type surrounded by undigested pieces of the fibrin gel matrix. The cells had many features of differentiated smooth muscle cells (fusiform, nonstriated, and uninucleated with the nucleus in the center of the cell), although the volume of the perinuclear space was small in comparison to cells in a normal muscle tissue. This suggests that the cells had not reached full maturation. As the gel contracted over time, cells increasingly aligned in a parallel array. Histological analysis showed a gradient of cell alignment as the entire gel began contracting (FIG. 6b). Fully contracted rings formed a ring with approximately 20 concentric cell layers. Ring diameters averaged 91.3±13.6 µm and ranged from 46.5-145.4 µm. The average cross-sectional area was calculated as 7532.9±2010.3 µm$^2$ and ranged from 1697.40-16604.90 µm$^2$. These measurements were used to determine the specific force of each IAS ring, defined as the maximal force produced divided by the cross-sectional area.

Example 3

Agonist-Induced Contraction and Relaxation of Bioengineered Sphincter Rings

Excitability and contractility of bioengineered IAS rings was measured using techniques adapted from previous work (Dennis et al., *In Vitro Cellular & Developmental Biology Animal* 36: 327-335, 2000. Dennis et al., *American Journal of Physiology Cell Physiology* 280: C288-C295, 2001). The diameter of the sphincter rings was measured and used to calculate cross-sectional area (CSA). The bioengineered sphincters were separated from their molds using forceps (FIG. 1 Panel E) and the minimum ring diameter was measured using a calibrated eyepiece and a 5× or 10× objective lens on an inverted microscope (Zeiss Axiovert 25, Thornwood, N.Y.). The cross section was circular, and therefore the CSA was calculated using the measured diameter.

To measure the passive baseline force, the differentiation media in the plate containing the bioengineered sphincter was replaced with 37° C. Krebs solution (NaCl (119 mM), KCl (4.6 mM), NaHCO$_3$ (15 mM), CaCl$_2$ (1.5 mM), MgCl$_2$ (1.2 mM), NaHCO$_3$ (1.2 mM), and glucose (11 mM)) and the plate was placed on a heated aluminum platform, which maintained a temperature of 37° C. until the testing was complete. For contractility measurements, one end of the bioengineered sphincter was anchored by a stainless steel pin (10 mm×0.1 mm diameter) to the PDMS substrate within the plate, while another stainless steel pin was bent in the shape of a hook and attached by canning wax to a force transducer (resolution of 1.4 µN and range of 2mN) as previously described (Dennis et al., *In Vitro Cellular & Developmental Biology Animal* 36: 327-335, 2000, Macpherson et al., *J Physiol* 500: 523-533, 1997) and as depicted in FIG. 1 (Panels F and G). The bioengineered sphincter was stretched approximately 50% of its resting length using a three-axis micromanipulator. The ring was allowed to sit for 20 minutes in order to reestablish a stable baseline level of force (Pb), which was measured as the average baseline passive force preceding stimulation.

All force measurements were collected at 100 samples/second for 60 seconds and recorded using a computer with LabVIEW data acquisition software (National Instruments, Austin, Tex.). A median filter of rank 2 was applied to all raw force data before being stored to minimize digitization noise without causing a phase delay for rapidly changing forces. The peak isometric force ($\Delta P$) was determined by subtracting the Pb from the total force values. Specific force (s$\Delta P$) was calculated by dividing $\Delta P$ by the CSA. Data analysis was done using LabVIEW and Microsoft Excel software programs. Each measurement was repeated at least three times and the mean value was recorded.

Contractions were induced in the rings by the addition of acetylcholine. Dose-response relationships of acetylcholine were investigated in the range of $10^{-6}$M to $10^{-10}$M. Incremental doses of acetylcholine were added after the maximal response of the preceding concentration and the establishment of a new baseline.

Relaxation response in the rings was induced by the addition of 8-Bromoadenosine 3':5'-Cyclic Monophosphate (8-br-cAMP). Maximal relaxation was achieved after approximately 4 minutes and therefore relaxation measurements are collective of four consecutive 1-minute data recordings.

Figure 3:
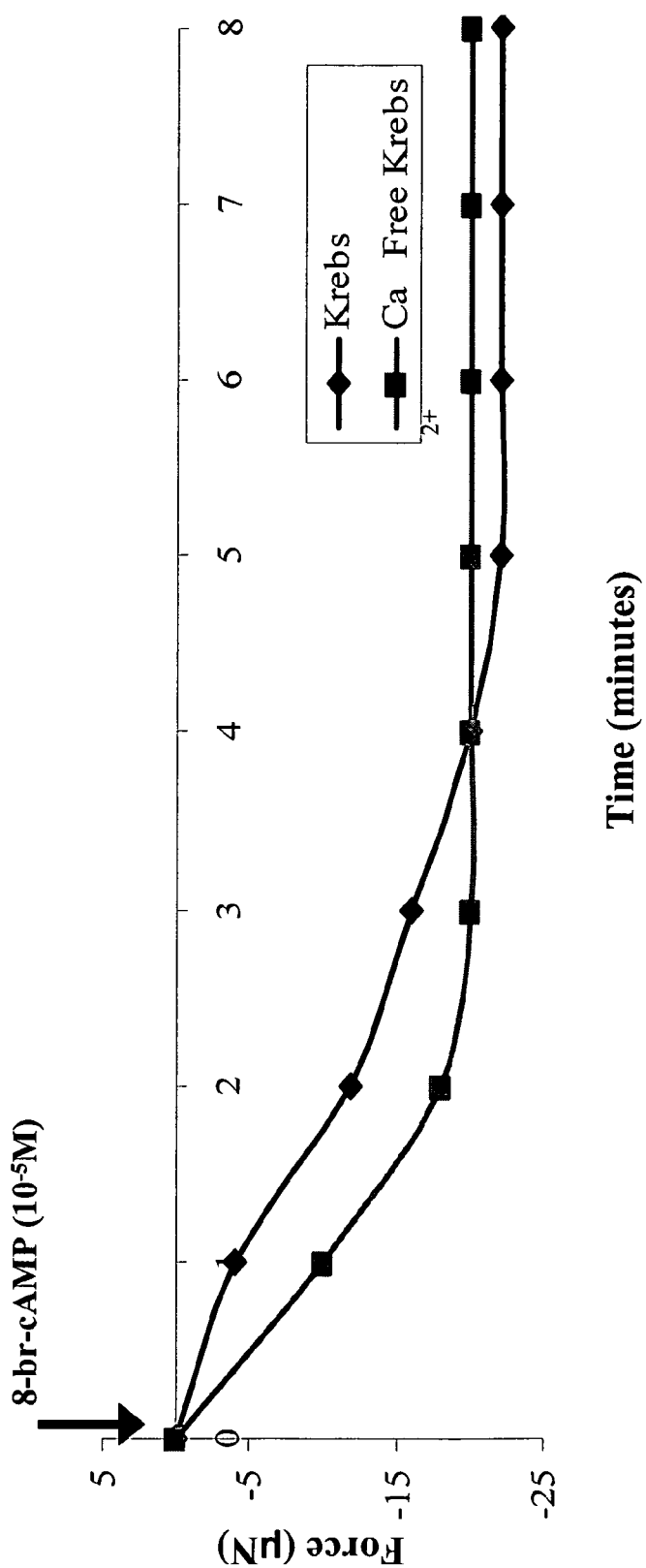
FIG. 3 depicts relaxation of the basal tone in IAS constructs: The effect of $10^{-5}$M 8-br-cAMP on IAS rings in Krebs versus 0 $Ca^{2+}$/2 mM EGTA Krebs buffer. Data points representing five successive readings of the decrease in resting force by IAS rings following the addition of 8-br-cAMP to the construct in Krebs versus 0 $Ca^{2+}$/2 mM EGTA Krebs buffer are depicted. IAS rings in both Krebs and 0 $Ca^{2+}$/2 mM EGTA Krebs buffer showed a maximum and sustained relaxation at approximately 3-4 minutes after the addition of $10^{-5}$M 8-br-cAMP. Thus, IAS rings responded functionally to 8-br-cAMP in a calcium-independent manner.
Figure 4:
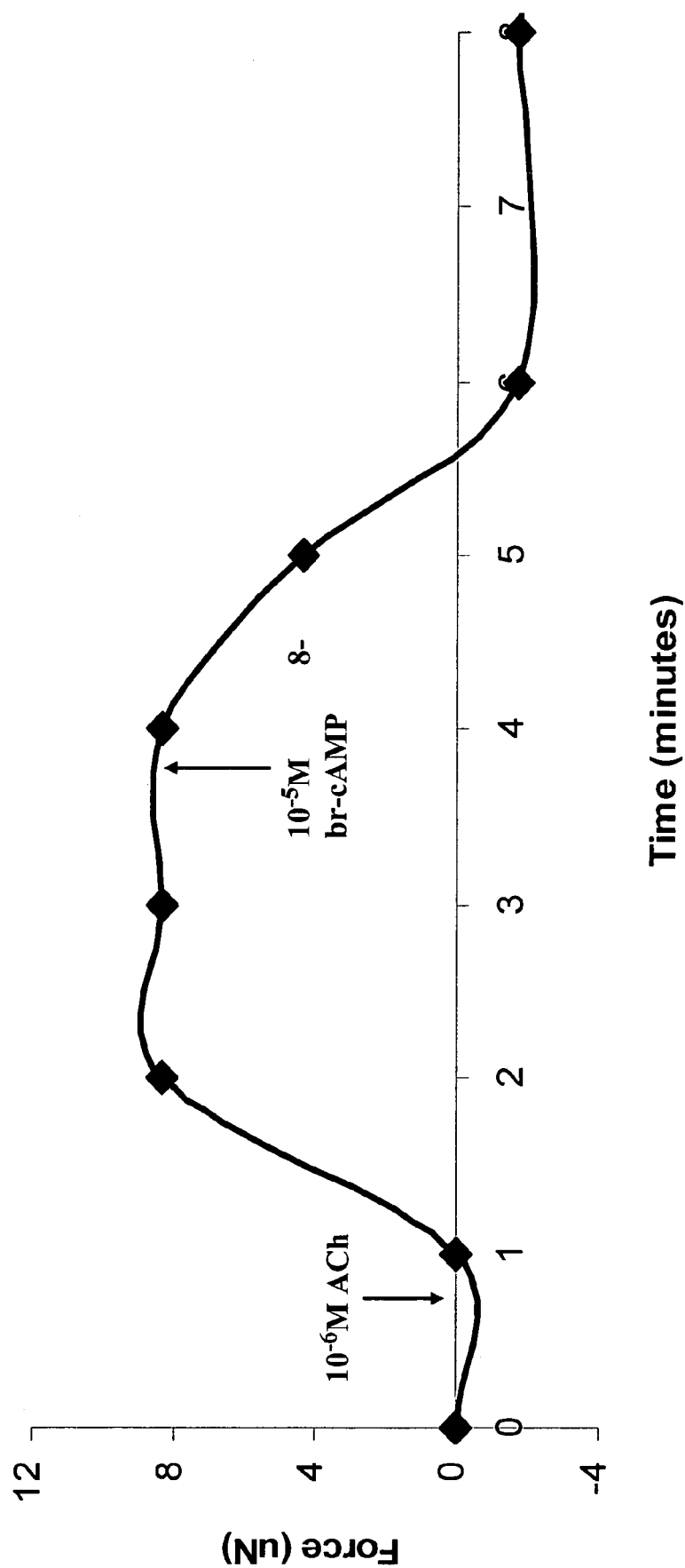
FIG. 4 depicts the effect of $10^{-6}$M acetylcholine and subsequent addition of $10^{-5}$M 8-br-cAMP on an IAS ring in Krebs buffer. Data points representing successive readings of the force generated by IAS rings after the addition of acetylcholine followed by addition of 8-br-cAMP are depicted. Arrows indicate the time at which the drug was added. Bioengineered IAS rings responded functionally in response to both acetylcholine and 8-br-cAMP. Addition of $10^{-5}$M 8-br-cAMP resulted in an immediate relaxation of acetylcholine induced contracted IAS rings.

Bioengineered IAS rings stimulated with $10^{-7}$M acetylcholine exhibited a peak ΔP within 30-60 of 9.8±3.8 μN seconds of force that was sustained for 4 minutes (FIG. 2). Maximal ΔP induced by acetylcholine stimulation was 33.7 μN resulting in a specific force (sΔP) of 2.8 kN/μm². Rings in 0 $Ca^{2+}$/2 mM EGTA Krebs (Krebs buffer without $CaCl_2$ and containing 2 mM EGTA) did not contract when stimulated with acetylcholine, demonstrating the calcium-dependence of the contractile response. Increasing the number of cells seeded in the construct did not result in increased force production by the three-dimensional sphincter rings. This suggests that the smooth muscle cells proliferated within the fibrin gel until they reached a constant confluence regardless of seeding density, due to density-dependent contact inhibition of cell division. Upon the addition of $10^{-5}$M 8-br-cAMP, IAS rings demonstrated a sustained relaxation response for approximately 4 minutes, resulting in the reestablishment of a new basal tone. Average ΔP for the rings after 4 minutes of incubation with $10^{-5}$ M 8-br-cAMP was −16.3±2.0 μN (FIG. 3). Stimulation with $10^{-5}$ 8-br-cAMP in $0Ca^{2+}$/2 mM EGTA Krebs also resulted in a relaxation response (−23±4 μN after 4 minutes), suggesting that relaxation was calcium-independent. Furthermore, addition of 8-br-cAMP-induced rapid relaxation of acetylcholine-induced contraction and force generation of IAS rings (FIG. 4).

Addition of 10-fold incremental doses of acetylcholine ranging from $10^{-10}$ M to $10^{-6}$ M induced a concentration-dependent contractile response, reaching a plateau at a concentration of $10^{-7}$ M (FIG. 2 Panel B). The dose-range of acetylcholine used here has been shown to produce a corresponding contractile response in isolated smooth muscle cells (Bitar et al., *Am J Physiol* 260: G537-G542, 1991; Bitar & Makhlouf *Am J Physiol* 250: G357-G360,1986; Moummi & Rattan *American Journal of Physiology Gastrointestinal and Liver Physiology* 255: G571-G578, 1988.) This similarity suggests that the bioengineered sphincter rings have the sensitivity of isolated single cells, which may be due to the lack the barriers present in muscle strips, such as innervating nerves, epithelial lining, and serosa.

Agonist-induced stimulation of bioengineered sphincter rings showed that these rings were functionally similar to smooth muscle in vivo. Furthermore, contraction of both single cells and rings was also calcium-dependent. This corresponds to the previously described acetylcholine-induced contraction of human IAS muscle strips (Glavind et al., *American Journal of Physiology Gastrointestinal and Liver Physiology* 265: G792-G798, 1993; Glavind et al., *American Journal of Physiology* 272: G1075-G1082, 1997. Knudsen et al., *American Journal of Physiology* 269: G232-G239, 1995). The bioengineered sphincter rings showed sustained relaxation in response to $10^{-5}$M 8-br-cAMP that was calcium-independent. Relaxation of smooth muscle in vivo is largely mediated by cAMP and is calcium-independent (Chakder & Rattan, *Am J Physiol* 264: G702-G707, 1993; Janis & Diamond *J Pharmacol Exp Ther* 211: 480-484, 1979; Moummi & Rattan *American Journal of Physiology Gastrointestinal and Liver Physiology* 255: G571-G578, 1988. Napoli et al., *Biochemistry* 19: 2515-2521, 1980). Bioengineered sphincter rings have the ability to contract and relax within minutes similar to the capacity seen in vivo.

Example 4

HSP27 Regenerated Contractile Force of Smooth Muscle Cells

Decreased association of actin with myosin and decreased association of tropomyosin with HSP27 in sphincteric smooth muscle cells from old rats (28-33 month old) was observed when compared to adult counterparts (18 months old). Whole cell lysates (WCL) from acetylcholine (0.1 μM) stimulated and unstimulated sphincteric smooth muscle cells of adult and old rats were extracted and immunoprecipitated as described previously (Somara et al, *Amer. J. Physiol.* 286(6): C1290-1301, 2004). Briefly, actin was immunoprecipited using an anti-actin antibody followed by immunoblotting with an anti-myosin antibody. A decrease in acetylcholine-induced association of actin with myosin in old rats sphincteric smooth muscle was demonstrated (175.32±10.12%, n=4, P<0.001 at 30 sec; 231.79±10.45%, n=4, P<0.001 at 4 minutes as compared to adult counterparts: 243.70±8.20%, n=4, P<0.001 at 30 seconds; 274.34±10.43%, n=4, P<0.001 at 4 minutes) In addition, tropomyosin was immunoprecipitated with anti-tropomyosin antibody followed by immunoblotting with anti-HSP27 antibody. This analysis showed a reduced acetylcholine-induced association of tropomyosin with HSP27 in old rats sphincteric smooth muscle (149.93±8.60%, n=4, P<0.001 at 30 sec; 223.21±7.46%, n=4, P<0.001 at 4 minutes as compared to adult counterpart: 218.67±5.48%, n=4, P<0.001 at 30 seconds; 268.39±6.38%, n=4, P<0.001 at 4 minutes).

Acetylcholine-induced contraction of isolated sphincteric smooth muscle cells was defined as the percent decrease in cell length compared to control. Adult rat IAS cells stimulated with $10^{-7}$M acetylcholine showed peak contraction at 30 seconds (44.7±1.34%) which was sustained for 4 minutes (40.65±1.43%, n=3). In old rats, $10^{-7}$M acetylcholine-induced contraction at 30 seconds was approximately 3-fold less forceful (12.8±4.4%) than adult rat cells. Furthermore, time-to-peak contraction was greater in old rat cells, as peak contraction had not been reached at 4 minutes (16.99±6.07%, n=3). After 30 second stimulation with $10^{-7}$M acetylcholine, a cell population profile also showed diminished contractility (less than 80 μM cell length) in old rat IAS cells (71%) o compared to adult cells (89%). In addition, after acetylcholine-induced contraction, there was a preponderance of longer cells and in old rats (24% above 80 μm) when compared to adult counterparts (17% above 80).

Bioengineered sphincter rings using smooth muscle cells isolated from IAS of adult and old rats were generated as described in Example 2 to study the molecular mechanism of aging on sphincteric smooth muscle. Agonist-induced stimulation of adult bioengineered sphincter rings showed functional similarities to smooth muscle in vivo. Upon stimulation with acetylcholine, both adult IAS rings and adult isolated IAS single cells exhibited a peak ΔP within 30-60 seconds after stimulation. Similarly, bioengineered adult IAS rings stimulated with $10^{-6}$M acetylcholine exhibited an average ΔP of 8.925±2.4 μN, which was sustained for 4 minutes. This corresponds to the previously described acetylcholine-induced contraction of human IAS muscle strips (16, 17, 27). These data are also similar to previously published contractile responses of isolated IAS cells and bioengineered IAS rings to acetylcholine Bioengineered sphincter rings made from old IAS cells generated approximately 50% less force than adult rings when stimulated with acetylcholine. Both, old isolated cells and old bioengineered rings, shared a decreased contractile response compared to corresponding adult counterparts. In old rings, maximal ΔP was usually generated between 5-20 minutes and in some cases taking up to 1 hour. As predicted by the contractile response of isolated old IAS cells, old IAS rings took more time to reach maximal ΔP than adult counterparts. Diminished contractility resulting from age has been seen previously in GI smooth muscle cells from old rats (Bitar, 2003). This decreased response can be correlated to the decreased acetylcholine-induced association of actin with myosin and a decreased acetylcholine-induced association of tropomyosin with HSP27 observed in sphincteric smooth muscle cells of old rats.

As decreased phosphorylation of HSP27 was attributed to decreased contraction and association of contractile proteins in colonic smooth muscle cells, the introduction of phosphorylated HSP27 into aged smooth muscle was investigated. Phosphomimic-HSP27 was introduced into the sphincteric smooth muscle cells from old rats. Biochemical studies using phosphomimic-HSP27 transfected sphincteric smooth muscle cells from old rats showed an increased acetylcholine-induced association of actin with myosin and increased acetylcholine-induced association of tropomyosin with HSP27. These data suggest that overexpression of HSP27 chaperone in old sphincteric smooth muscle may reinstate the contractile response that is affected in age-related sphincter dysfunction. To test this hypothesis on a physiological level, bioengineered sphincter rings were made from phosphomimic-HSP27 transfected-IAS smooth muscle cells of old rats and the contractile response was assessed.

Stable bioengineered sphincter rings generated from phosphomimic-HSP27 transfected sphincteric smooth muscle cells of old rat showed rapidity and increased magnitude in force generation. As shown in FIG. 5, transfected rings stimulated with $10^{-6}$ M acetylcholine generated a force of 9.97±4.5 µN, which was similar in magnitude to the force generated in adult rings (8.925±2.4 µN) and significantly greater than old rings (5.55±1.1 µN). Transfected rings showed a maximal ΔP between 30 seconds-2 minutes, which is considerably faster than the time-to-peak force seen in old rings (5 minutes-1 hour). HSP27 transfected rings showed an increase in force generation and response time as compared to age-matched rings. Transfection of old IAS cells with HSP27 can reinstate contractile associations at the molecular level, leading to increased functionality at the tissue level. This demonstrates that the effects of aging, leading to decreased contractility of smooth muscle in the IAS or other sphincters, can be corrected.

To further investigate phospho-HSP27-induced reinstatement of smooth muscle cell contractile function, sphincter smooth muscle cells isolated from old rats IAS were transfected with phosphomimic-HSP27 as described previously. Whole cells lysates were extracted and immunoprecipitated as described previously (Somara et al, *Amer. J. Physiol.* 286(6): C1290-1301, 2004). Actin was immunoprecipitated with an anti-actin antibody followed by immunoblotting with anti-myosin antibody showed an increased acetylcholine-induced association of actin with myosin in phosphomimic-HSP27 transfected sphincter smooth muscle cells (263.57+9.16%, n=4, P<0.001 at 30 seconds; 279.74+6.00%, n=4, P<0.001 at 4 minutes as compared to age-matched counterparts (175.32+10.12%, n=4, P<0.001 at 30 seconds; 231.79+10.45%, n=4, P<0.001 at 4 minutes). In addition, tropomyosin was immunoprecipitation with an anti-tropomyosin antibody followed by immunoblotting with anti-HSP27 antibody, which demonstrated an increased acetylcholine-induced association of tropomyosin with HSP27 in phosphomimic-HSP27 transfected sphincter smooth muscle cells (235.18+5.37%, P<0.001 at 30 seconds; 256.25+6.54%, P<0.001 at 4 minutes; n=4 as compared to age-matched counterparts: 149.93+8.60%, P<0.001 at 30 seconds; 223.21+7.46%, P<0.001 at 4 minutes; n=4).

Example 5

Development of Three-Dimensional Physiological Model of Smooth Muscle Tissue

To develop a three dimensional physiological model of the smooth muscle cells in vitro, isolated colonic smooth muscle cells were used. Smooth muscle cells isolated from the colon of rabbits were seeded in a fibrin-based tissue construct as described in detail in Example 2. In this construct, the smooth muscle cells migrated and self-assembled in circumferential alignment. As the cells proliferated, the fibrin gel shrunk and contracted around a 5 mm diameter SYLGARD mold, resulting in a 3-D cylindrical ring of colonic tissue (smooth muscle ring).

The bioengineered colon smooth muscle rings consistently exhibited spontaneous phasic contraction similar to spontaneous contractile patterns observed in vivo. Upon stimulation with acetylcholine, the bioengineered colon smooth muscle rings showed a calcium-dependent peak contraction at 30 seconds, which was sustained for 4 minutes. Addition of 10-fold incremental doses of acetylcholine, ranging from $10^{-10}$M to $10^{-6}$M, resulted in a concentration-dependent contractile response. Maximal ΔP induced by acetylcholine stimulation was 17.8 µN, resulting in a specific force (sΔP) of 7.1 kN/µm2. Thus, bioengineered smooth muscle ring of the invention demonstrate physiological functionality, including spontaneous contractile behavior, and may be used in the elucidation of the mechanisms causing smooth muscle dysfunction such as colon malfunction.

What is claimed is:

1. A method of generating a bioengineered sphincter comprising the steps of growing smooth muscle cells in an extracellular matrix under conditions in which the smooth muscle cells contract in response to an agonist and said extracellular matrix covers polydimethyl siloxane-coated cell culture vessel and a polydimethyl siloxane-coated cylindrical mold, said polydimethyl siloxane-coated cylindrical mold is within said polydimethyl siloxane-coated cell culture vessel.

2. The method of claim 1 wherein the smooth muscle cells are grown in an extracellular matrix under conditions in which the smooth muscle cells relax in response to a relaxant.

3. The method of claim 1 wherein the extracellular matrix is fibrin.

4. The method of claim 1 wherein mammalian the smooth muscle cells are isolated from an internal anal sphincter or a gastrointestinal sphincter.

* * * * *

UNITED STATES PATENT AND TRADEMARK OFFICE
CERTIFICATE OF CORRECTION

PATENT NO. : 7,368,279 B2 Page 1 of 1
APPLICATION NO. : 11/286544
DATED : May 6, 2008
INVENTOR(S) : Khalil N. Bitar et al.

It is certified that error appears in the above-identified patent and that said Letters Patent is hereby corrected as shown below:

At Column 30, line 45, after "growing" insert --mammalian--.

At Column 30, line 59, after "wherein" insert --the--.

At Column 30, line 59, delete "the" after "mammalian".

Signed and Sealed this

Thirtieth Day of September, 2008

JON W. DUDAS
*Director of the United States Patent and Trademark Office*